United States Patent
Guiles et al.

(10) Patent No.: US 6,964,652 B2
(45) Date of Patent: Nov. 15, 2005

(54) LEFT VENTRICULAR CONDUITS AND METHODS FOR DELIVERY

(75) Inventors: Marvin Guiles, Stow, MA (US); Gerald Melsky, Lexington, MA (US)

(73) Assignee: Percardia, Inc., Merrimack, NH (US)

( * ) Notice: Subject to any disclaimer, the term of this patent is extended or adjusted under 35 U.S.C. 154(b) by 31 days.

(21) Appl. No.: 10/617,176

(22) Filed: Jul. 11, 2003

(65) Prior Publication Data

US 2004/0106931 A1 Jun. 3, 2004

Related U.S. Application Data

(62) Division of application No. 09/630,385, filed on Aug. 1, 2000, now Pat. No. 6,638,237.
(60) Provisional application No. 60/147,211, filed on Aug. 4, 1999.

(51) Int. Cl.[7] ............................................... A61M 5/00
(52) U.S. Cl. ...................................................... 604/117
(58) Field of Search .......................................... 604/117

(56) References Cited

U.S. PATENT DOCUMENTS

| | | | |
|---|---|---|---|
| 3,971,363 A | 7/1976 | Fletcher et al. | |
| 4,503,568 A | 3/1985 | Madras | |

(Continued)

FOREIGN PATENT DOCUMENTS

| | | |
|---|---|---|
| AU | 757647 B2 | 2/2003 |
| EP | 0 732 088 A2 | 9/1996 |

(Continued)

OTHER PUBLICATIONS

US 6,331,185, 12/2001, Gambale et al. (withdrawn)

Katherine S. Tweden, Frazier Eales, J. Douglas Cameron, Jerry C. Griffin, Eric E. Solien & Mark B. Knudson; "Ventriculocoronary Artery Bypass (VCAB), a Novel Approach to Myocardial Revascularization"; Feb. 2000; Article #2000–4653.

Banning G. Lary, Antonio Camelo, Roger W. Sherman & Thomas J. Noto; "Myocardial Revascularization Experiments using the Epicardium"; Archives of Surgery.; Jan. 1969; pp. 69–72; vol. 98; American Medical Association; U.S.A.

(Continued)

Primary Examiner—J. Casimer Jacyna
(74) Attorney, Agent, or Firm—Finnegan, Henderson Farabow, Garrett & Dunner LLP

(57) ABSTRACT

Conduits are provided to direct blood flow from the left ventricle to a coronary artery at a location distal to a blockage in the coronary artery. Threaded and nonthreaded conduits are delivered using a guidewire delivered through the posterior and anterior walls of a coronary artery and into the heart wall. A dilator may be provided over the guidewire into the heart wall, and the conduit delivered over the dilator. An introducer sleeve may be provided over the dilator into the heart wall, the dilator removed, and the conduit delivered through the introducer sleeve. A hollow needle also may be inserted into the posterior and anterior walls of the coronary artery prior to inserting the guidewire. A depth measuring tool may determine the appropriate length of the conduit prior to delivery. The depth measuring tool can include the hollow needle with an access port on a proximal end of the needle and an opening on the distal end of the needle in flow communication with the access port so that when the needle is inserted through the heart wall and into the heart chamber, blood flow through the opening.

20 Claims, 21 Drawing Sheets

U.S. PATENT DOCUMENTS

| | | | |
|---|---|---|---|
| 4,733,665 A | 3/1988 | Palmaz | |
| 4,769,029 A | 9/1988 | Patel | |
| 4,953,553 A | 9/1990 | Tremulis | |
| 4,995,857 A | 2/1991 | Arnold | |
| 5,035,702 A | 7/1991 | Taheri | |
| 5,135,467 A | 8/1992 | Citron | |
| 5,190,058 A | 3/1993 | Jones et al. | |
| 5,193,546 A | 3/1993 | Shaknovich | |
| 5,226,889 A | 7/1993 | Sheiban | |
| 5,258,008 A | 11/1993 | Wilk | |
| 5,287,861 A | 2/1994 | Wilk | |
| 5,292,309 A | 3/1994 | Van Tassel et al. | |
| 5,330,486 A | 7/1994 | Wilk | |
| 5,344,426 A | 9/1994 | Lau et al. | |
| 5,385,541 A | 1/1995 | Kirsch et al. | |
| 5,389,096 A | 2/1995 | Aita et al. | |
| 5,409,019 A | 4/1995 | Wilk | |
| 5,423,744 A | 6/1995 | Gencheff et al. | |
| 5,423,851 A | 6/1995 | Samuels | |
| 5,429,144 A | 7/1995 | Wilk | |
| 5,443,497 A | 8/1995 | Venbrux | |
| 5,456,694 A | 10/1995 | Marin et al. | |
| 5,456,712 A | 10/1995 | Maginot | |
| 5,456,714 A | 10/1995 | Owen | |
| 5,470,320 A | 11/1995 | Tiefenbrun et al. | |
| 5,527,337 A | 6/1996 | Stack et al. | |
| 5,554,119 A | 9/1996 | Harrison et al. | |
| 5,578,075 A | 11/1996 | Dayton | |
| 5,593,434 A | 1/1997 | Williams | |
| 5,609,626 A | 3/1997 | Quijano et al. | |
| 5,611,778 A | 3/1997 | Brinon | |
| 5,618,299 A | 4/1997 | Khosravi et al. | |
| 5,643,278 A | 7/1997 | Wijay | |
| 5,655,548 A | 8/1997 | Nelson et al. | |
| 5,662,124 A | 9/1997 | Wilk | |
| 5,676,670 A | 10/1997 | Kim | |
| 5,733,267 A | 3/1998 | Del Toro | |
| 5,755,682 A | 5/1998 | Knudson et al. | |
| 5,758,663 A | 6/1998 | Wilk et al. | |
| 5,787,933 A | 8/1998 | Russ et al. | |
| 5,797,920 A | 8/1998 | Kim | |
| 5,807,384 A | 9/1998 | Mueller | |
| 5,810,836 A | 9/1998 | Hussein et al. | |
| 5,810,871 A | 9/1998 | Tuckey et al. | |
| 5,824,038 A | 10/1998 | Wall | |
| 5,824,071 A | 10/1998 | Nelson et al. | |
| 5,830,222 A | 11/1998 | Makower | |
| 5,843,163 A | 12/1998 | Wall | |
| 5,851,232 A | 12/1998 | Lois | |
| 5,855,597 A | 1/1999 | Jayaraman | |
| 5,865,723 A | 2/1999 | Love | |
| 5,876,373 A | 3/1999 | Giba et al. | |
| 5,876,419 A | 3/1999 | Carpenter et al. | |
| 5,878,751 A | 3/1999 | Hussein et al. | |
| 5,885,259 A | 3/1999 | Berg | |
| 5,893,848 A | 4/1999 | Negus et al. | |
| 5,908,028 A | 6/1999 | Wilk | |
| 5,908,029 A | 6/1999 | Knudson et al. | |
| 5,922,022 A | 7/1999 | Nash et al. | |
| 5,925,012 A | 7/1999 | Murphy-Chutorian et al. | |
| 5,931,848 A | 8/1999 | Saadat | |
| 5,935,119 A | 8/1999 | Guy et al. | |
| 5,935,161 A | 8/1999 | Robinson et al. | |
| 5,935,162 A | 8/1999 | Dang | |
| 5,938,632 A | 8/1999 | Ellis | |
| 5,944,019 A | 8/1999 | Knudson et al. | |
| 5,961,548 A | 10/1999 | Shmulewitz | |
| 5,968,064 A | 10/1999 | Selmon et al. | |
| 5,968,093 A | 10/1999 | Kranz | |
| 5,971,993 A | 10/1999 | Hussein et al. | |
| 5,976,153 A | 11/1999 | Fischell et al. | |
| 5,976,155 A | 11/1999 | Foreman et al. | |
| 5,976,159 A | 11/1999 | Bolduc et al. | |
| 5,976,169 A | 11/1999 | Imran | |
| 5,976,178 A | 11/1999 | Goldsteen et al. | |
| 5,976,181 A | 11/1999 | Whelan et al. | |
| 5,976,182 A | 11/1999 | Cox | |
| 5,976,192 A | 11/1999 | McIntyre et al. | |
| 5,976,650 A | 11/1999 | Campbell et al. | |
| 5,979,455 A | 11/1999 | Maginot | |
| 5,980,530 A | 11/1999 | Willard et al. | |
| 5,980,533 A | 11/1999 | Holman | |
| 5,980,548 A | 11/1999 | Evans et al. | |
| 5,980,551 A | 11/1999 | Summers et al. | |
| 5,980,552 A | 11/1999 | Pinchasik et al. | |
| 5,980,553 A | 11/1999 | Gray et al. | |
| 5,980,566 A | 11/1999 | Alt et al. | |
| 5,984,955 A | 11/1999 | Wisselink | |
| 5,984,956 A | 11/1999 | Tweden et al. | |
| 5,984,963 A | 11/1999 | Ryan et al. | |
| 5,984,965 A | 11/1999 | Knapp et al. | |
| 5,989,207 A | 11/1999 | Hughes | |
| 5,989,263 A | 11/1999 | Shmulewitz | |
| 5,989,287 A | 11/1999 | Yang et al. | |
| 5,993,481 A | 11/1999 | Marcade et al. | |
| 5,993,482 A | 11/1999 | Chuter | |
| 5,997,525 A | 12/1999 | March et al. | |
| 5,997,563 A | 12/1999 | Kretzers | |
| 5,997,573 A | 12/1999 | Quijano et al. | |
| 5,999,678 A | 12/1999 | Murphy-Chutorian et al. | |
| 6,001,123 A | 12/1999 | Lau | |
| 6,004,261 A | 12/1999 | Sinofsky et al. | |
| 6,004,347 A | 12/1999 | McNamara et al. | |
| 6,004,348 A | 12/1999 | Banas et al. | |
| 6,007,543 A | 12/1999 | Ellis et al. | |
| 6,007,575 A | 12/1999 | Samuels | |
| 6,007,576 A | 12/1999 | McClellan | |
| 6,010,449 A | 1/2000 | Selmon et al. | |
| 6,010,530 A | 1/2000 | Goicoechea | |
| 6,017,365 A | 1/2000 | Von Oepen | |
| 6,026,814 A | 2/2000 | LaFontaine et al. | |
| 6,029,672 A * | 2/2000 | Vanney et al. | 128/898 |
| 6,035,856 A | 3/2000 | LaFontaine et al. | |
| 6,036,677 A | 3/2000 | Javier, Jr. et al. | |
| 6,036,697 A | 3/2000 | DiCaprio | |
| 6,039,721 A | 3/2000 | Johnson et al. | |
| 6,042,581 A | 3/2000 | Ryan et al. | |
| 6,045,565 A | 4/2000 | Ellis et al. | |
| 6,053,911 A | 4/2000 | Ryan et al. | |
| 6,053,924 A | 4/2000 | Hussein | |
| 6,053,942 A | 4/2000 | Eno et al. | |
| 6,056,743 A | 5/2000 | Ellis et al. | |
| 6,067,988 A | 5/2000 | Mueller | |
| 6,068,638 A | 5/2000 | Makower | |
| 6,071,292 A | 6/2000 | Makower et al. | |
| 6,076,529 A | 6/2000 | Vanney et al. | |
| 6,080,163 A | 6/2000 | Hussein et al. | |
| 6,080,170 A | 6/2000 | Nash et al. | |
| 6,092,526 A | 7/2000 | LaFontaine et al. | |
| 6,093,166 A | 7/2000 | Knudson et al. | |
| 6,093,177 A | 7/2000 | Javier, Jr. et al. | |
| 6,093,185 A | 7/2000 | Ellis et al. | |
| 6,095,997 A | 8/2000 | French et al. | |
| 6,102,941 A | 8/2000 | Tweden et al. | |
| 6,106,538 A | 8/2000 | Shiber | |
| 6,110,201 A | 8/2000 | Quijano et al. | |
| 6,113,630 A | 9/2000 | Vanney et al. | |
| 6,113,823 A | 9/2000 | Eno | |
| 6,117,165 A | 9/2000 | Becker | |
| 6,120,520 A | 9/2000 | Saadat et al. | |
| 6,123,682 A | 9/2000 | Knudson et al. | |

| | | |
|---|---|---|
| 6,126,649 A | 10/2000 | Van Tassel et al. |
| 6,126,654 A | 10/2000 | Giba et al. |
| 6,132,451 A | 10/2000 | Payne et al. |
| 6,139,541 A | 10/2000 | Vanney et al. |
| 6,152,141 A | 11/2000 | Stevens et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,171,251 B1 | 1/2001 | Mueller et al. |
| 6,171,303 B1 | 1/2001 | Ben-Haim et al. |
| 6,182,668 B1 | 2/2001 | Tweden et al. |
| 6,186,972 B1 | 2/2001 | Nelson et al. |
| 6,190,353 B1 | 2/2001 | Makower et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,324 B1 | 3/2001 | Crittenden |
| 6,200,310 B1 | 3/2001 | Ben-Haim et al. |
| 6,200,311 B1 | 3/2001 | Danek et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,719 B1 | 9/2001 | Garberoglio |
| 6,290,728 B1 | 9/2001 | Phelps et al. |
| 6,302,875 B1 | 10/2001 | Makower et al. |
| 6,302,892 B1 | 10/2001 | Wilk |
| 6,306,125 B1 | 10/2001 | Parker et al. |
| 6,322,548 B1 | 11/2001 | Payne et al. |
| 6,330,884 B1 | 12/2001 | Kim |
| 6,331,178 B1 | 12/2001 | Loeb et al. |
| 6,344,027 B1 | 2/2002 | Goll |
| 6,350,248 B1 | 2/2002 | Knudson et al. |
| 6,352,543 B1 | 3/2002 | Cole |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B2 | 11/2002 | Herweck et al. |
| 6,482,220 B1 | 11/2002 | Mueller |
| 6,491,689 B1 | 12/2002 | Ellis et al. |
| 6,491,707 B2 | 12/2002 | Makower et al. |
| 6,506,408 B1 | 1/2003 | Palasis |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |
| 6,524,324 B1 | 2/2003 | Mueller et al. |
| 6,544,230 B1 | 4/2003 | Flaherty et al. |
| 6,559,132 B1 | 5/2003 | Holmer |
| 6,561,998 B1 | 5/2003 | Roth et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B2 | 6/2003 | LaFontaine et al. |
| 6,579,311 B1 | 6/2003 | Makower |
| 6,582,444 B2 | 6/2003 | Wilk |
| 6,585,650 B1 | 7/2003 | Solem |
| 6,587,718 B2 | 7/2003 | Talpade |
| 6,589,164 B1 | 7/2003 | Flaherty |
| 6,599,304 B1 | 7/2003 | Selmon et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,026 B1 | 9/2003 | Palasis et al. |
| 6,613,081 B2 | 9/2003 | Kim et al. |
| 6,616,675 B1 | 9/2003 | Evard et al. |
| 6,635,214 B2 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Briefs et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |

| Patent/Publication | Date | Inventor |
|---|---|---|
| 6,660,024 B1 | 12/2003 | Flaherty et al. |
| 6,669,691 B1 | 12/2003 | Taimisto |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,425 B2 | 3/2004 | Gambale et al. |
| 6,709,427 B1 | 3/2004 | Nash et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,746,426 B1 | 6/2004 | Flaherty et al. |
| 6,746,464 B1 | 6/2004 | Makower |
| 6,748,258 B1 | 6/2004 | Mueller et al. |
| 6,774,155 B2 | 8/2004 | Martakos et al. |
| 6,774,278 B1 | 8/2004 | Ragheb et al. |
| 6,786,929 B2 | 9/2004 | Gambale et al. |
| 6,802,858 B2 | 10/2004 | Gambale et al. |
| 6,808,498 B2 | 10/2004 | Laroya et al. |
| 2001/0000041 A1 | 3/2001 | Selmon et al. |
| 2001/0003985 A1 | 6/2001 | LaFontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | AKin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0045928 A1 | 4/2002 | Boekstegers |
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0077566 A1 | 6/2002 | Laroya et al. |
| 2002/0077654 A1 | 6/2002 | Javier, Jr. et al. |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095206 A1 | 7/2002 | Addonizio et al. |
| 2002/0100484 A1 | 8/2002 | Hall et al. |
| 2002/0103495 A1 | 8/2002 | Cole |
| 2002/0111672 A1 | 8/2002 | Kim et al. |
| 2002/0123698 A1 | 9/2002 | Garibotto et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0144696 A1 | 10/2002 | Sharkawy et al. |
| 2002/0161383 A1 | 10/2002 | Akin et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0073973 A1 | 4/2003 | Evans et al. |
| 2003/0078561 A1 | 4/2003 | Gambale et al. |
| 2003/0097172 A1 | 5/2003 | Shalev et al. |
| 2003/0100920 A1 | 5/2003 | Akin et al. |
| 2003/0105514 A1 | 6/2003 | Phelps et al. |
| 2003/0114872 A1 | 6/2003 | Mueller et al. |
| 2003/0120195 A1 | 6/2003 | Milo et al. |
| 2003/0149126 A1 | 8/2003 | Martakos et al. |
| 2003/0149474 A1 | 8/2003 | Becker |
| 2003/0158573 A1 | 8/2003 | Gittings et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0195606 A1 | 10/2003 | Davidson et al. |
| 2003/0204160 A1 | 10/2003 | Kamm et al. |
| 2003/0212413 A1 | 11/2003 | Wilk |
| 2003/0216679 A1 | 11/2003 | Wolf et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0006301 A1 | 1/2004 | Sell et al. |
| 2004/0015225 A1 | 1/2004 | Kim et al. |
| 2004/0019348 A1 | 1/2004 | Stevens et al. |
| 2004/0044392 A1 | 3/2004 | Von Oepen |
| 2004/0058097 A1 | 3/2004 | Weder |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0106931 A1 | 6/2004 | Guiles et al. |
| 2004/0113306 A1 | 6/2004 | Rapacki et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0133154 A1 | 7/2004 | Flaherty et al. |
| 2004/0133225 A1 | 7/2004 | Makower |
| 2004/0147869 A1 | 7/2004 | Wolf et al. |
| 2004/0158143 A1 | 8/2004 | Flaherty et al. |
| 2004/0158227 A1 | 8/2004 | Nash et al. |
| 2004/0167444 A1 | 8/2004 | Laroya et al. |
| 2004/0168691 A1 | 9/2004 | Sharkawry et al. |
| 2004/0186507 A1 | 9/2004 | Hall et al. |
| 2004/0186557 A1 | 9/2004 | Gambale et al. |
| 2004/0186587 A1 | 9/2004 | Ahem |
| 2004/0210304 A1 | 10/2004 | Seguin et al. |
| 2004/0219180 A1 | 11/2004 | Gambale et al. |
| 2004/0220598 A1 | 11/2004 | Bolduc et al. |
| 2004/0225355 A1 | 11/2004 | Stevens |
| 2004/0236418 A1 | 11/2004 | Stevens |

FOREIGN PATENT DOCUMENTS

| | | |
|---|---|---|
| EP | 0 792 624 A1 | 9/1997 |
| EP | 0 797 957 A1 | 10/1997 |
| EP | 0 797 958 A1 | 10/1997 |

| | | | | | | |
|---|---|---|---|---|---|---|
| EP | 0 799 604 A1 | 10/1997 | | WO | WO 98/57592 A1 | 12/1998 |
| EP | 0 801 928 A1 | 10/1997 | | WO | WO 99/07296 A1 | 2/1999 |
| EP | 0 815 798 A2 | 1/1998 | | WO | WO 99/08624 A1 | 2/1999 |
| EP | 0 824 903 | 2/1998 | | WO | WO 99/21490 A1 | 5/1999 |
| EP | 0 829 239 A1 | 3/1998 | | WO | WO 99/21510 A1 | 5/1999 |
| EP | 0 836 834 A2 | 4/1998 | | WO | WO 99/22655 A1 | 5/1999 |
| EP | 0 853 921 A2 | 7/1998 | | WO | WO 99/22658 A1 | 5/1999 |
| EP | 0 858 779 A1 | 8/1998 | | WO | WO 99/25273 A1 | 5/1999 |
| EP | 0 876 796 A2 | 11/1998 | | WO | WO 99/27985 A1 | 6/1999 |
| EP | 0 876 803 A2 | 11/1998 | | WO | WO 99/32051 | 7/1999 |
| EP | 0 888 750 A1 | 1/1999 | | WO | WO 99/35977 A1 | 7/1999 |
| EP | 0 895 752 A1 | 2/1999 | | WO | WO 99/35979 A1 | 7/1999 |
| EP | 0 903 123 | 3/1999 | | WO | WO 99/35980 A1 | 7/1999 |
| EP | 0 904 745 | 3/1999 | | WO | WO 99/36000 A1 | 7/1999 |
| EP | 0 934 728 A2 | 8/1999 | | WO | WO 99/36001 A1 | 7/1999 |
| EP | 0 955 017 | 11/1999 | | WO | WO 99/37218 | 7/1999 |
| EP | 0 955 019 | 11/1999 | | WO | WO 99/38459 A2 | 8/1999 |
| EP | 962 194 | 12/1999 | | WO | WO 99/40853 A1 | 8/1999 |
| EP | 1 020 166 A1 | 7/2000 | | WO | WO 99/40868 A1 | 8/1999 |
| EP | 1 027 870 A1 | 8/2000 | | WO | WO 99/40963 A1 | 8/1999 |
| EP | 1 088 564 A1 | 4/2001 | | WO | WO 99/44524 A2 | 9/1999 |
| EP | 1 097 676 A1 | 5/2001 | | WO | WO 99/47071 | 9/1999 |
| EP | 1 166 721 A2 | 1/2002 | | WO | WO 99/47078 | 9/1999 |
| EP | 0 959 815 A1 | 12/2002 | | WO | WO 99/48427 | 9/1999 |
| EP | 1 112 097 A1 | 6/2003 | | WO | WO 99/48545 A1 | 9/1999 |
| EP | 0 954 248 B1 | 9/2004 | | WO | WO 99/48549 A2 | 9/1999 |
| EP | 1 115 452 B1 | 11/2004 | | WO | WO 99/49790 | 10/1999 |
| EP | 1 477 202 A2 | 11/2004 | | WO | WO 99/49793 A1 | 10/1999 |
| EP | 1 107 710 B1 | 12/2004 | | WO | WO 99/49910 A2 | 10/1999 |
| GB | 2 316 322 B | 10/1998 | | WO | WO 99/51162 A1 | 10/1999 |
| WO | WO 94/16229 | 8/1994 | | WO | WO 99/52481 | 10/1999 |
| WO | WO 96/32972 A1 | 10/1996 | | WO | WO 99/53863 A1 | 10/1999 |
| WO | WO 96/35469 A1 | 11/1996 | | WO | WO 99/55406 A1 | 11/1999 |
| WO | WO 96/39962 A1 | 12/1996 | | WO | WO 99/60941 A1 | 12/1999 |
| WO | WO 96/39964 A1 | 12/1996 | | WO | WO 99/62430 A1 | 12/1999 |
| WO | WO 96/39965 A1 | 12/1996 | | WO | WO 00/09195 A1 | 2/2000 |
| WO | WO 97/13463 A1 | 4/1997 | | WO | WO 00/1518 | 3/2000 |
| WO | WO 97/13471 | 4/1997 | | WO | WO 00/12029 A1 | 3/2000 |
| WO | WO 97/18768 | 5/1997 | | WO | WO 00/13722 A1 | 3/2000 |
| WO | WO 97/27893 A1 | 8/1997 | | WO | WO 00/15146 A1 | 3/2000 |
| WO | WO 97/27897 A1 | 8/1997 | | WO | WO 00/15147 A1 | 3/2000 |
| WO | WO 97/27898 A1 | 8/1997 | | WO | WO 00/15149 A1 | 3/2000 |
| WO | WO 97/31590 | 9/1997 | | WO | WO 00/15275 A2 | 3/2000 |
| WO | WO 97/32551 A1 | 9/1997 | | WO | WO 00/16848 A1 | 3/2000 |
| WO | WO 97/41916 | 11/1997 | | WO | WO 00/18302 A2 | 4/2000 |
| WO | WO 97/43961 A1 | 11/1997 | | WO | WO 00/18323 A2 | 4/2000 |
| WO | WO 98/02099 | 1/1998 | | WO | WO 00/18325 A1 | 4/2000 |
| WO | WO 98/03118 A1 | 1/1998 | | WO | WO 00/18326 A1 | 4/2000 |
| WO | WO 98/06356 A1 | 2/1998 | | WO | WO 00/18331 A2 | 4/2000 |
| WO | WO 98/08456 | 3/1998 | | WO | WO 00/18462 A2 | 4/2000 |
| WO | WO 98/10714 A1 | 3/1998 | | WO | WO 00/21436 A1 | 4/2000 |
| WO | WO 98/16161 A1 | 4/1998 | | WO | WO 00/21461 A2 | 4/2000 |
| WO | WO 98/17185 | 4/1998 | | WO | WO 00/21463 A1 | 4/2000 |
| WO | WO 99/17683 A1 | 4/1998 | | WO | WO 00/24449 A1 | 5/2000 |
| WO | WO 98/19607 | 5/1998 | | WO | WO 00/33725 A2 | 6/2000 |
| WO | WO 98/24373 A1 | 6/1998 | | WO | WO 00/35376 A1 | 6/2000 |
| WO | WO 98/25533 A1 | 6/1998 | | WO | WO 00/36997 A1 | 6/2000 |
| WO | WO 98/25549 | 6/1998 | | WO | WO 00/41632 A1 | 7/2000 |
| WO | WO 98/38916 A1 | 9/1998 | | WO | WO 00/41633 A1 | 7/2000 |
| WO | WO 98/38925 A1 | 9/1998 | | WO | WO 00/43051 A1 | 7/2000 |
| WO | WO 98/38939 A1 | 9/1998 | | WO | WO 00/45711 A1 | 8/2000 |
| WO | WO 98/38941 A1 | 9/1998 | | WO | WO 00/45886 A2 | 8/2000 |
| WO | WO 98/39038 A1 | 9/1998 | | WO | WO 00/49952 A1 | 8/2000 |
| WO | WO 98/44869 | 10/1998 | | WO | WO 00/49954 A2 | 8/2000 |
| WO | WO 98/46115 A2 | 10/1998 | | WO | WO 00/49956 A1 | 8/2000 |
| WO | WO 98/46119 A1 | 10/1998 | | WO | WO 00/54660 A1 | 9/2000 |
| WO | WO 98/49964 A1 | 11/1998 | | WO | WO 00/54661 A1 | 9/2000 |
| WO | WO 98/53759 | 12/1998 | | WO | WO 00/56224 A1 | 9/2000 |
| WO | WO 98/55027 | 12/1998 | | WO | WO 00/56225 A1 | 9/2000 |
| WO | WO 98/57590 A1 | 12/1998 | | WO | WO 00/56387 A1 | 9/2000 |
| WO | WO 98/57591 A1 | 12/1998 | | WO | WO 00/66007 A1 | 11/2000 |

| | | |
|---|---|---|
| WO | WO 00/66009 A1 | 11/2000 |
| WO | WO 00/66035 A1 | 11/2000 |
| WO | WO 00/69345 A1 | 11/2000 |
| WO | WO 00/69504 A1 | 11/2000 |
| WO | WO 00/71195 A1 | 11/2000 |
| WO | WO /10341 A2 | 2/2001 |
| WO | WO 01/08566 A1 | 2/2001 |
| WO | WO 01/08602 A1 | 2/2001 |
| WO | WO 01/10340 A1 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/17440 A1 | 3/2001 |
| WO | WO 01/17456 A1 | 3/2001 |
| WO | WO 01/23016 A1 | 4/2001 |
| WO | WO 01/41657 A1 | 6/2001 |
| WO | WO 01/49187 A1 | 7/2001 |
| WO | WO 01/68158 A1 | 9/2001 |
| WO | WO 01/70133 A2 | 9/2001 |
| WO | WO 01/72239 A2 | 10/2001 |
| WO | WO 01/78801 A2 | 10/2001 |
| WO | WO 01/82803 A1 | 11/2001 |
| WO | WO 01/82837 A2 | 11/2001 |

OTHER PUBLICATIONS

Ladislav Kuzela & George E. Miller, Jr.; "Experimental evaluation of direct transventricular revascularization"; Journal of Thoracic and Cardiovascular Surgery; Jun. 1969; pp. 770–773; vol. 57, No. 6; The C.V. Mosby Company; St. Louis, MO.

C. Massimo & L. Boffi; "Myocardial, Revascularization by a New Method of Carrying Blood Directly From the Left Ventricular Cavity into the Coronary Circulation"; Journal of Thoracic Surgery; Aug. 1957; pp. 257–264; vol. 34; U.S.A.

Isam N. Anabtawi, Hubert F. Reigler, & Robert G. Ellison; "Experimental evaluation of myocardial tunnelization as a method of myocardial revascularization"; Journal of Thoracic and Cardiovascular Surgery; Nov. 1969; pp. 638–646; vol. 58, No. 5; The C.V. Mosby Company; St. Louis, MO.

Ian Munro & Peter Allen; "The possibility of myocardial revascularization by creation of a left ventriculocoronary artey listula"; The Journal of Thoracic and Cardiovascular Surgery; Jul. 1969; pp. 25–32; vol. 58, No. 1; The C.V. Mosby Company; St. Louis, MO.

Julio C. Palmaz, Francisco Garcia, Randy R. Sibbitt, Frenin O. Tio, David T. Kopp, Wayne Schwesinger, Jack L. Lancaster & Peter Chang; "Expandable Intrahepatic Portacaval Shunt Stents in Dogs with Chronic Portal Hypertension"; American Journal of Roentgenology; Dec. 1986; pp. 1251–1254; vol. 147; The American Roengen Ray Society; U.S.A.

Julio C. Palmaz, Randy R. Sibbitt, Stewart R. Reuter, Francisco Garcia & Fremin O. Tio; "Expandable Intrahepatic Portacaval Shunt Stents; Early Experience in the Dog"; American Journal of Roentgenology; Oct. 1985; pp. 821–825; vol. 145; The American Roentgen Ray Society, U.S.A.

Garrett Lee, Richard M. Ikeda, Jerold Theis, Daniel Stobbe, Claire Ogata, Henry Lui, Robert L. Reis, & Dean T. Mason; "Effects of laser irradiation delivered by flexible fiberoptic system on the left ventricular internal myocardium"; American Heart Journal; Sep. 1983; pp. 587–590; vol. 106, No. 3; The C.V. Mosby Company; St. Louis, MO.

Texas Heart Institute Journal, "Transmyocardial Laser Revascularization," D. Cooley, M.D., et al., pp. 220–224, vol. 21, No. 3, 1994.

American Journal of Physiology, "Transmural Myocardial Perfusion During Restricted Coronary Inflow in the Awake Dog," R. Bache, et al., pp. H645–651, vol. 232, No. 6 ISSN–0002–9513.

The Annals of Thoracic Surgery, "Myocardial Canalization," A. Khazei, M.D., et al., vol. 6, No. 2, Aug. 1968.

Surgical Forum, "Proceedings of the 24th Annual Sessions of the Forum on Fundamental Surgical Problems," 54th Cllincal Congress of the American College of Surgeons, Chicago, Illinois, Oct., 1968, pp. 156–159, American College of Surgeons, Chicago, Illinois.

Anne Bohning, Kenneth Jochim & Louis N. Katz; "The Thebesian Vessels as a Source of Nourishment for the Myocardium"; American Journal of Physiology; 1933; pp. 183–200; vol. 106; American Physological Society; U.S.A.

Alfred Goldman, Seymour M. Greenstone, Fred S. Preuss, Sherman H. Strauss & En–Shu Chang; "Experimental Methods for Producing a Collateral Circulation to the Heart Directly from the Left Ventricle"; Journal of Thoracic Surgery; Mar. 1956; pp. 364–374; vol. 31, No. 3; U.S.A.

Banning G. Lary & Roger W. Sherman; "A method for creating a coronary–myocardial artery"; Surgery; Jun. 1966; pp. 1061–1604; vol. 59, No. 6; The C.V. Mosby Company; St. Louis, MO.

Akio Wakayabashi, Solomon T. Little, Jr. & John E. Connolly; "Myocardial Boring for the Ischemic Heart"; Archives of Surgery; Nov. 1967; pp. 743–752; vol. 95; American Medical Association; U.S.A.

Robert J. Gardner, Benjamin L. Plybon & Herbert E. Warden; "An Experimental Anatomic Study of Indirect Myocardial Revascularization"; Journal of Surgical Research; 1971; pp. 243–247; vol. 11; Academic Press; U.S.A.

Frank M. Galioto, Milton J. Reitman, Arnold J. Slovis & Irving A. Sarot; "Right coronary artery to left ventricle fistula; A case report and discussion"; American Heart Journal; Jul. 1971; pp. 93–97; vol. 82, No. 1; The C.V. Mosby Company; St. Louis, MO.

Joseph P. Archie Jr.; "Intramyocardial Pressure: Effect of Preload on Transmural Distribution of Systolic Coronary Blood Flow"; The American Journal of Cardiology; Jun. 1975; pp. 904–911; vol. 35; U.S.A.

L. Levinsky, T.Z. Lajos, A.B. Lee, Jr., C. Espersen, & G. Schimert; "The Revival of the Horeshoe Graft (Side–toSide Saphenous–Vein–to–Aorta Anastomosis"; The Thoracic and Cardiovascular Surgeon; Oct. 1979; pp. 322–324; vol. 27; No. 5; Georg Thieme Publishers; Stuttgart, Germany.

S. Sultan Ahmed, Bunyad Haider & Timothy J. Regan; "Silent left coronary artery–cameral fistula: probable cause of myocardial ischemia"; American Heart Journal; Oct. 1982; pp. 869–870; vol. 104, No. 4, pt. 1; The C.V. Mosby Company; St. Louis, MO.

Goetz M. Richter, Gerd Noeldge, Julio C. Palmaz, Martin Roessle, Volker Slegerstetter, Martina Franke, Wolfgang Gerok, Werner Wenz & Edward Farthman; "Transjugular Intrahepatic Portacaval Stent Shunt: Preliminary Clinical Results"; Radiology; Mar. 1990; pp. 1027–1030; vol. 174, No. 3, Pt. 2; The Radiological Society of North America; Oak Brook, IL.

Gerald Zemel, Barry T. Katzen, Gary J. Becker, James F. Benenati & D. Skip Sallee; "Percutaneous Transjugular Portosystemic Shunt"; The Journal of the American Medical Association; Jul. 1991; pp. 390–393; vol. 266, No. 3; American Medical Association; U.S.A.

Medical Industry Today Headline News; "Eclipse Gets OK to Pump Catheter Marketing in Europe"; Jul. 17, 1998; pp. 1–2; Article #07179802, Article is 349 words long; Medical Data International, Inc.; Santa Ana, CA.

Medical Industry Today Headline News; "Sales Dive, Losses Soar in 2Q for CardioGenesis"; Jul. 17, 1998; pp. 1–2; Article #07179808, Article is 560 words long; Medical Data International, Inc.; U.S.A.

Howard A. Cohen & Marco Zenati; "Alternative Approaches to Coronary Revascularization";Current International Cardiology Reports; 1999; pp. 138–146; vol. 1; Current Science, Inc.; U.S.A.

Stephen N. Oesterle, Nicolaus Reifart, Motoya Hayase, Eugene, Haputmann, Reginald Low, Raimund Erbel, Michael Hause, Olaf Dirsch, Gerhard C. Schuler, Renu Virmani & Alan C. Yeung; "Catheter–Based Coronary Bypass: A development Update"; Catheterization and Cardiovascular Interventions; 2003; pp. 212.218; vol. 58; Wiley–Liss, Inc.; U.S.A.

Terminal Disclaimer dated Nov. 1, 2004, filed in copending U.S. Appl. No. 09/534,038; pp.1–3

Amendment dated Nov. 1, 2004, filed in copending U.S. Appl. No. 09/534,038, pp. 1–11.

Office Action dated Jul. 2, 2004, in copending U.S. Appl. No. 09/534,038, (13 pages).

Amendment dated Feb. 5, 2004, filed in copending U.S. Appl. No. 09/534,038, pp. 1–9.

Amendment and Response to Restriction Requirement dated Mar. 4, 2003, filed in copending U.S. Appl. No. 09/534,038, pp. 1–10.

Office Action dated Nov. 5, 2003, in copending U.S. Appl. No. 09/534,038, (23 pages).

Second Supplemental Amendment dated Jul. 16, 2003, filed in copending U.S. Appl. No. 09/534,038, pp. 1–2.

Supplemental Amendment dated Jun. 20, 2003, filed in copending U.S. Appl. No. 09/534,038, pp. 1–8.

Office Action dated Feb. 4, 2003, in copending U.S. Appl. No. 09/534,038, (9 pages).

Supplemental Preliminary Amendment and Claim of Priority dated Aug. 31, 2000, filed in copending U.S. Appl. No. 09/534,038, pp. 1–2.

Preliminary Amendment dated Jun. 19, 2000, filed in copending U.S. Appl. No. 09/534,038, pp. 1–6.

* cited by examiner

PULL OUT FORCES OF VARIOUS THREADED SCREWS

| DESCRIPTION | THREADS PER INCH | HEIGHT OF THREADS | SHAFT DIAMETER | AVERAGE PULL OUT FORCE (LBS) |
|---|---|---|---|---|
| DRYWALL SCREW | 15 | 0.023 | 0.093 | 1.80 |
| DRYWALL SCREW | 15 | 0.024 | 0.088 | 1.80 |
| DRYWALL SCREW | 8 | 0.028 | 0.122 | 1.75 |
| HEX BOLT | 30 | 0.015 | 0.132 | <0.250 |
| SHEET METAL SCREW | 10 | 0.032 | 0.156 | 3.00 |

*FIG. 14*

PULL OUT FORCES OF BARBED SHUNTS

| DESCRIPTION (ALL BARBS ARE ANNULAR) | NUMBER OF BARBS | BARB SPACING | BARB WIDTH (IN) | BARB DIAMETER | BARB HEIGHT (IN) | AVERAGE REMOVAL FORCE (LBS) |
|---|---|---|---|---|---|---|
| ANGLED BARBS FACING ONE DIRECTION | 3 | 0.140 | 0.040 | 0.110 | 0.0065 | 0.38 |
| CONTINUOUS ANGLED BARBS, NO SPACING BETWEEN EACH ONE | 8 | NONE | 0.068 | 0.109 | 0.0055 | 0.42 |
| ANGLED BARBS FACING ONE DIRECTION, FLANGE AT ONE END (TESTED IN DIFFERENT HEART) | 6 | NONE | 0.085 | 0.108 | 0.0065 | 0.13 |
| FLAT BARBS | 4 | 0.062 | 0.049 | 0.108 | 0.0060 | 0.29 |
| FLAT BARBS | 2 | 0.140 | 0.054 | 0.110 | 0.0065 | 0.25 |
| STENT ANGLED AT ONE END, FLAT BARBS, FLANGE AT OPPOSITE END (TESTED IN DIFFERENT HEART) | 3 | 0.094 | 0.097 | 0.109 | 0.0035 | <.13 |
| CONTROL SAMPLE | NONE | NONE | NONE | NONE | NONE | ~0 |

*ALL INSERTION FORCES ARE APPROXIMATELY 1.0 LB
*THE APPROXIMATE WALL THICKNESS OF THE LEFT VENTRICLE IS .67-.84 IN, NEAR THE APEX OF THE HEART IT IS APPROXIMATELY .51 IN

*FIG. 15*

PULL THROUGH FORCES FOR FLANGES THROUGH ARTERIAL WALL

| DESCRIPTION | WIDTH (IN) | LENGTH (IN) | AVERAGE PULL THROUGH FORCE (LBS) |
|---|---|---|---|
| SHALLOW FLANGE, BARBED STENT, NO SPACES BETWEEN EACH BARB | 0.114 | 0.169 | 0.50 |
| SHALLOW FLANGE, FLAT BARBED STENT, OPPOSITE END ANGLED | 0.097 | 0.132 | 0.50 |
| DEEP FLANGE, FLAT STENT | 0.108 | 0.159 | 1.00 |
| VERY LONG AND DEEP FLANGE, FLAT STENT | 0.109 | 0.195 | 1.50 |
| FLAT STENT WITH ANGLED END, FLANGE TUBE SHAPED WITH OPENING IN THE MIDDLE | 0.094 | 0.182 | 0.75 |
| CIRCULAR FLANGE, FLAT STENT | | 0.169 R | 0.75 |

*FIG. 16*

LEFT VENTRICULAR CONDUITS AND METHODS FOR DELIVERY

CROSS REFERENCE TO RELATED APPLICATIONS

This application is a divisional of U.S. application Ser. No. 09/630,385, filed Aug. 1, 2000, now U.S. Pat. No. 6,638,237, which claims the benefits of priority of U.S. Provisional Application No. 60/147,211, filed Aug. 4, 1999, both of which are incorporated herein by reference.

FIELD OF THE INVENTION

The present invention relates to an apparatus for bypassing a blocked or stenosed blood vessel segment, and, more particularly, to an apparatus and method for delivering a conduit between the coronary artery and the left ventricle of the heart.

BACKGROUND OF THE INVENTION

Coronary artery disease is a major problem in the U.S. and throughout the world. Coronary arteries as well as other blood vessels frequently become clogged with plaque which, at the very least, can reduce blood and oxygen flow to the heart muscle (myocardium), and may impair the efficiency of the heart's pumping action, and can lead to heart attack (myocardial infarction) and death. In some cases, these coronary arteries can be unblocked through non-invasive techniques such as balloon angioplasty. In more difficult cases, a surgical bypass of the blocked vessel is necessary.

In a coronary bypass operation, one or more venous segments are inserted between the aorta and the coronary artery, or, alternatively, the distal end of an internal mammary artery is anastomosed to the coronary artery at a site distal to the stenosis or occlusion. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass graft (CABG) surgery, however, is a very intrusive procedure which is expensive, time-consuming, and traumatic to the patient. The operation requires an incision through the patient's sternum (sternotomy), and that the patient be placed on a heart-lung bypass pump so that the heart can be operated on while not beating. A saphenous vein graft is harvested from the patient's leg, another highly invasive procedure, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type or location of the blockage or stenosis, or due to the risk of emboli.

Thus, there is a need for an improved coronary bypass system which is less traumatic to the patient.

SUMMARY OF THE INVENTION

Briefly stated, the methods and apparatus described and illustrated herein generally relate to direct coronary revascularization, wherein a conduit or opening is provided from the left ventricle to the coronary artery, oftentimes the left anterior descending (LAD), to provide blood flow directly therethrough. These methods and apparatus are particularly useful when a blockage partially or completely obstructs the coronary artery, in which case the bypass conduit or opening is positioned distal to the blockage. More preferably, conduits are provided to direct blood flow from the left ventricle to a coronary artery at a location distal to a blockage in the coronary artery. The conduits may be threaded to facilitate insertion into a patient's heart wall and to control the depth of insertion. Threaded and nonthreaded conduits are preferably delivered using a guidewire approach. In this approach, the guidewire is placed through a needle that is inserted into the left ventricle. After the guidewire is placed, the needle is removed. In one embodiment, a dilator is provided over the guidewire into the heart wall, and the conduit is delivered over the dilator. In another embodiment, an introducer sleeve is provided over the dilator into the heart wall, the dilator is removed, and the conduit is delivered through the introducer sleeve. A depth measuring tool is preferably used to determine the appropriate length of the conduit prior to delivery. In another embodiment, a feature can be included on the end of the introducer sleeve that engages with the arterial wall, and when pulled back, distends the artery. The conduit can then be advanced until the deployable flanges seat against the bottom of the artery.

BRIEF DESCRIPTION OF THE DRAWINGS

FIG. 14 is a table of the pull out forces of various threaded conduits that may be used according to certain embodiments of the present invention.

FIG. 15 is a table of pull out forces of various barbed conduits that may be used according to certain embodiments of the present invention.

FIG. 16 is a table of push-through forces of various conduits having flanges that may be used according to certain embodiments of the present invention.

DETAILED DESCRIPTION OF THE PREFERRED EMBODIMENT

Figure 1:
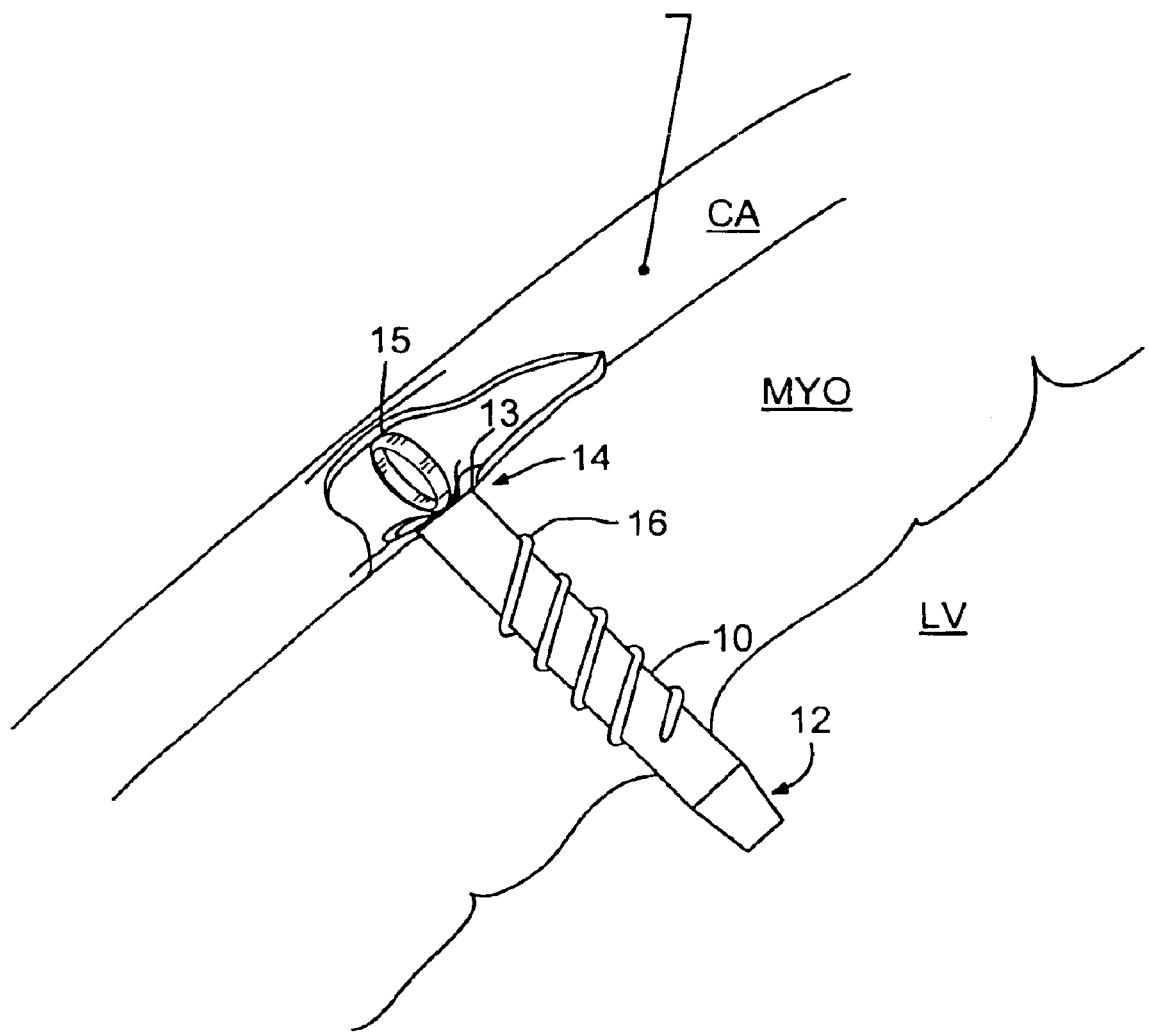
FIG. 1 is a schematic side view of a threaded conduit inserted into a heart wall of a patient between the left ventricle and a coronary artery according to a preferred embodiment of the present invention.

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the rest of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

FIG. 1 illustrates schematically a threaded conduit according to one preferred embodiment of the present invention. The conduit 10 is preferably an elongate tubular body having a proximal end 12 and a distal end 14 and a lumen (not shown) extending therethrough. The proximal end 12 preferably tapers to the desired internal diameter (ID) of the device. The majority of the conduit 10 is threaded with threads 16 to facilitate insertion of the conduit into the heart, as described below. In one preferred embodiment, the entire body of the conduit 10 is threaded except for the proximal tip 12 of the conduit. The conduit may or may not have flange-like features 13 on its distal end that engage with the artery lumen. In addition, the conduit may or may not have a ring 15 for engaging the artery and allowing blood to pass therethrough. FIG. 1 illustrates the conduit 10 as implanted in a patient, wherein the conduit preferably extends between the left ventricle LV, through the myocardium MYO and into the coronary artery CA.

Figure 2:
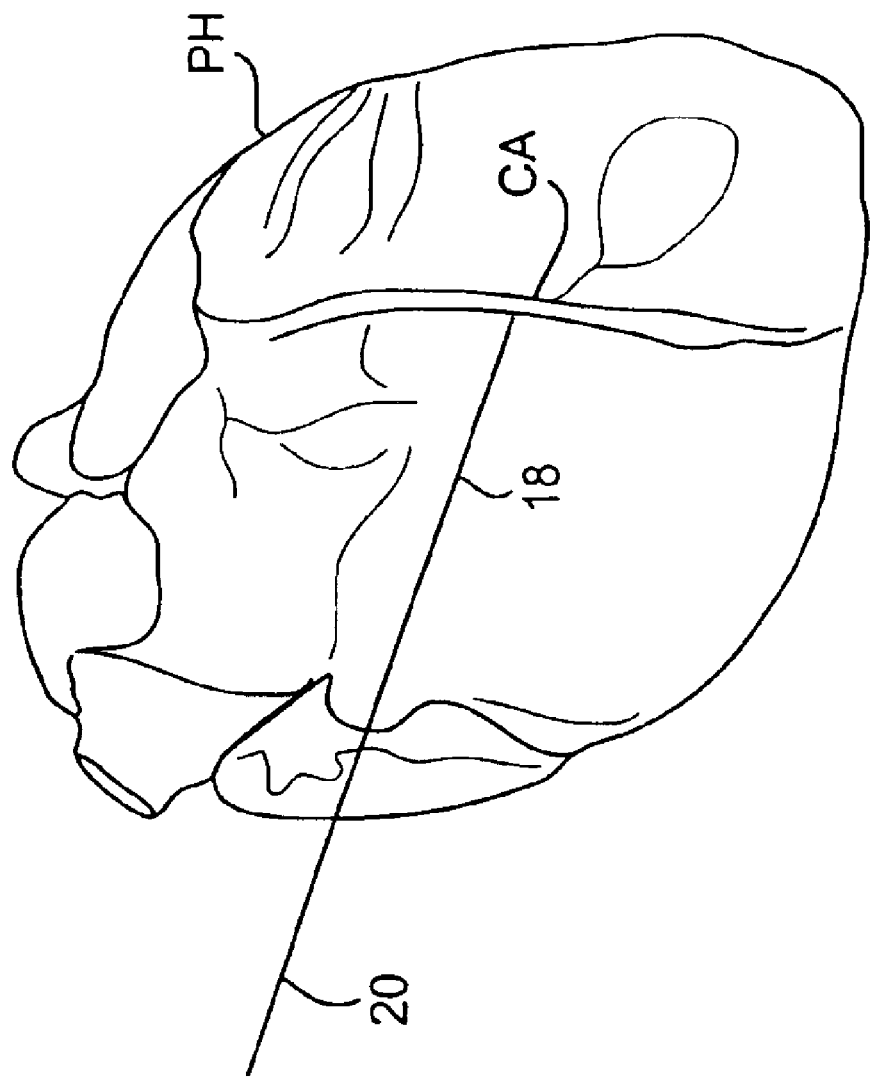
FIG. 2 is a side view of a heart having a needle inserted through a coronary artery to the left ventricle, and a guidewire inserted therethrough.
Figure 2A:
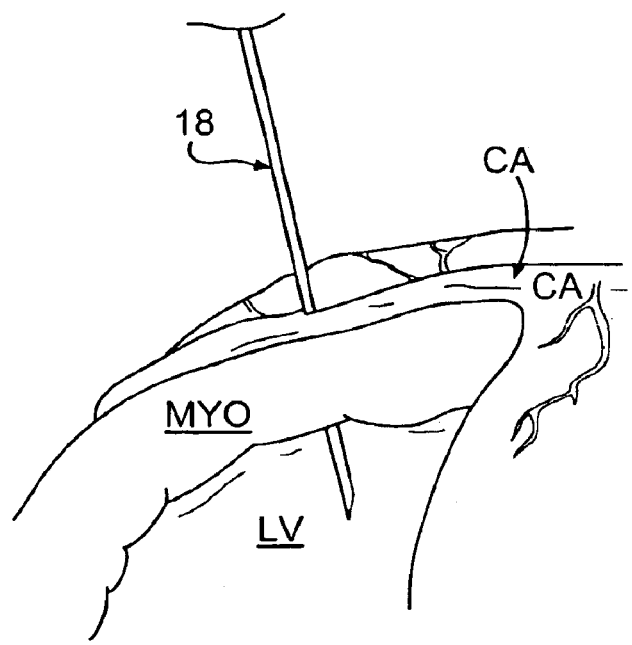
FIG. 2A is a side view showing a needle being inserted through a coronary artery into the left ventricle.

FIGS. 2–5 illustrate one embodiment for delivering the conduit 10 into a patient. Although these figures illustrate a pig heart, it will be appreciated that the methods described herein apply to human hearts as well. To deliver the conduit 10 into the myocardium of the heart PH, a needle 18, as shown in FIG. 2, is first inserted through the heart wall into the left ventricle (also illustrated in FIG. 2A). The needle 18 is preferably hollow, and is preferably inserted through an anterior wall and then a posterior wall of the coronary artery CA. After the needle is inserted, access to the left ventricle may be verified. If it is necessary to relocate the needle, the needle leaves only a very small hole upon removal.

Figure 2B:
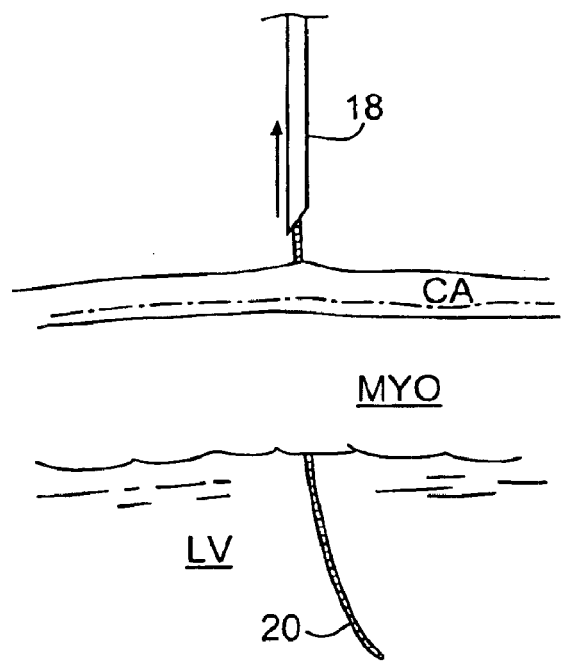
FIG. 2B is a side view of a guidewire inserted through the needle of FIG. 2A, with the needle being removed.

As shown in FIG. 2, after the needle is placed in the left ventricle, a guidewire 20 is inserted into the lumen in the needle. The guidewire is preferably a 0.014 guidewire, which extends into the left ventricle through the needle. After placement of the guidewire the needle is removed, as illustrated in FIG. 2B.

Figure 3:
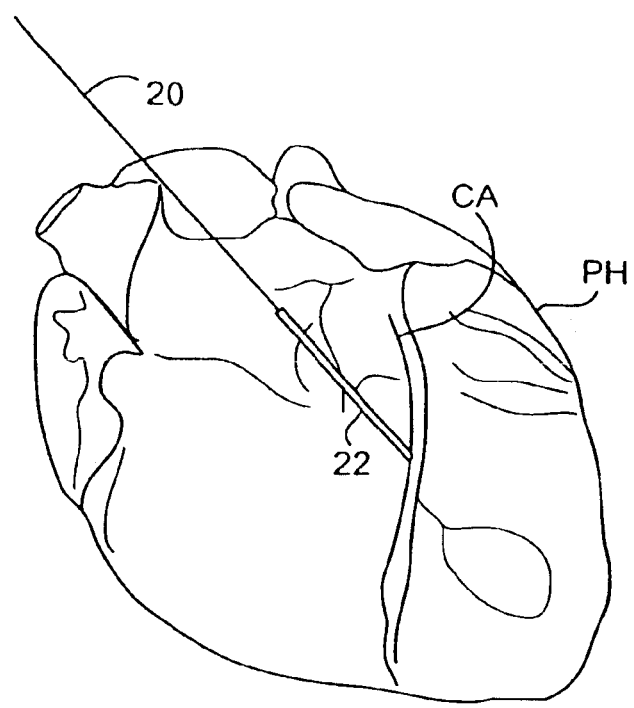
FIG. 3 is a side view of a dilator being inserted over the guidewire of FIG. 2.
Figure 3A:
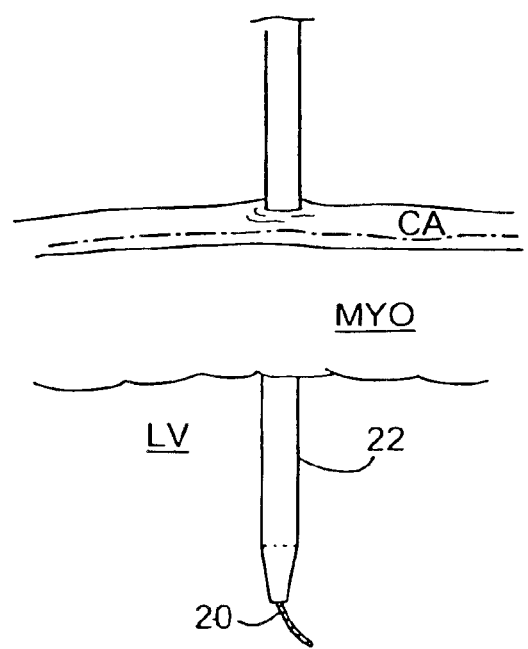
FIG. 3A is a side view of an introducer being advanced over the guidewire of FIG. 2B.

As shown in FIGS. 3 and 3A, a dilator or introducer 22 is preferably inserted over the guidewire and into the heart until the dilator reaches the left ventricle. Upon reaching this position, the guidewire 20 is removed from the heart.

Figure 4:
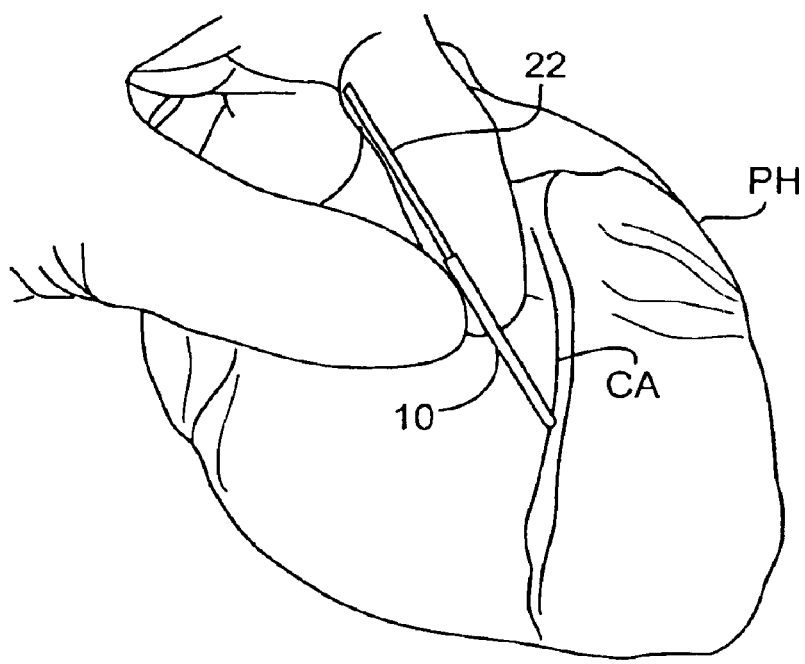
FIG. 4 is a side view of a threaded conduit being inserted over the dilator of FIG. 3.
Figure 4A:
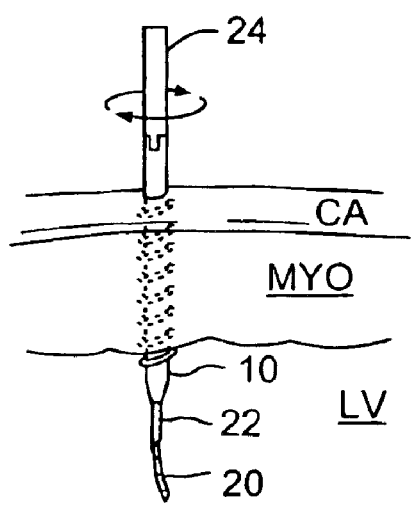
FIG. 4A is a side view of a tool being used to insert a threaded conduit inserted over the dilator of FIG. 3A.

As shown in FIGS. 4 and 4A, a threaded conduit 10, such as described with respect to FIG. 1 above, is placed over the dilator. The non-threaded tapered tip 16 (shown in FIG. 1) of the conduit is inserted into the coronary artery. The conduit 10 is then preferably pulled back to open the artery. The first few threads are then advanced by twisting the threaded conduit. The conduit 10 may be in the form of a shunt.

Figure 5:
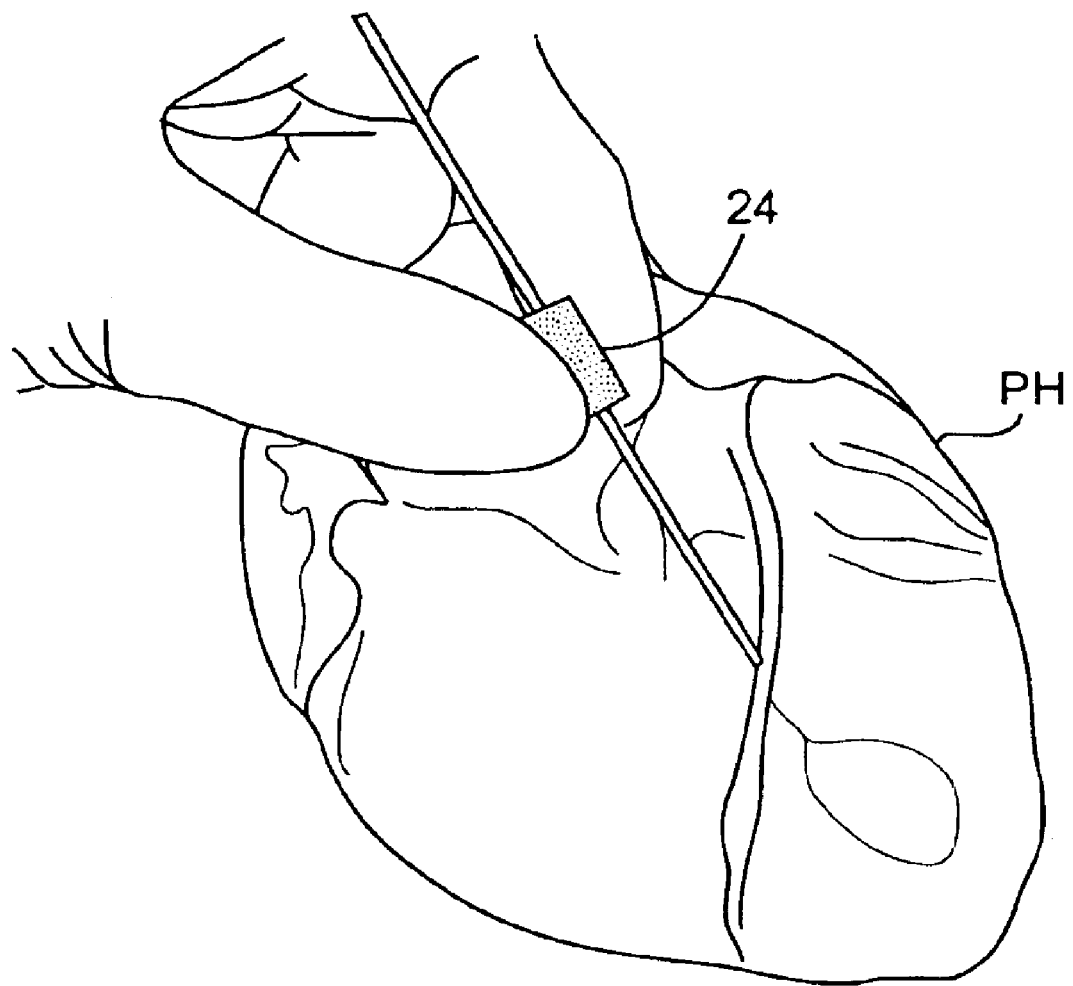
FIG. 5 is a side view showing the threaded conduit of FIG. 4 being advanced into position.

A tool 24 is then used to advance the conduit 10 to the proper depth, as shown in FIGS. 5 and 4A. More preferably, the tool 24 mates with the distal end of the conduit in order to turn the conduit. Because the conduit 10 is threaded, the tool 24 can easily adjust the conduit to a desired depth. After the conduit 10 reaches the desired depth, the tool and the dilator are removed, leaving the conduit 10 in place.

Figure 5A:
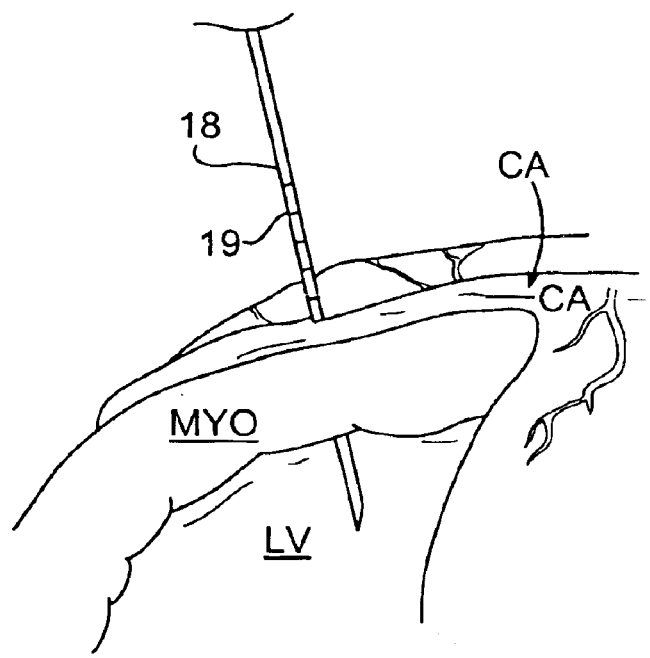
FIGS. 5A–5D are the side views of FIGS. 2A, 2B, 3A and 4A, more particularly showing features included on the needle, introducer and deployment tool that aid in determining the proper deployment depth.
Figure 5B:
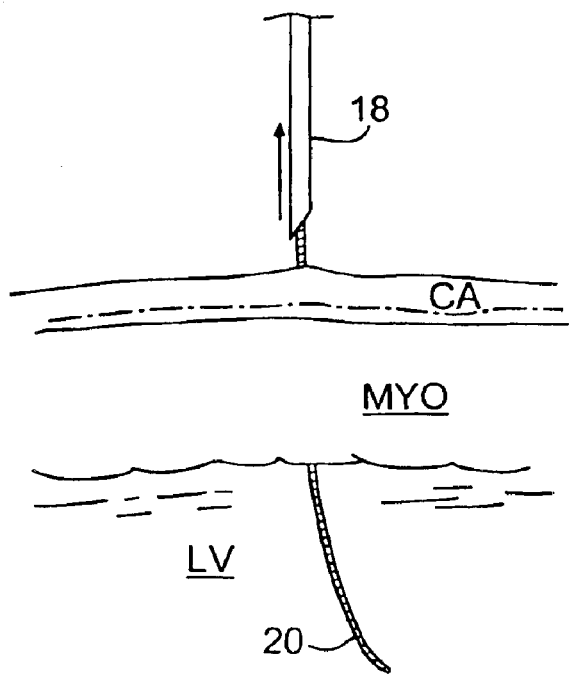
Figure 5C:
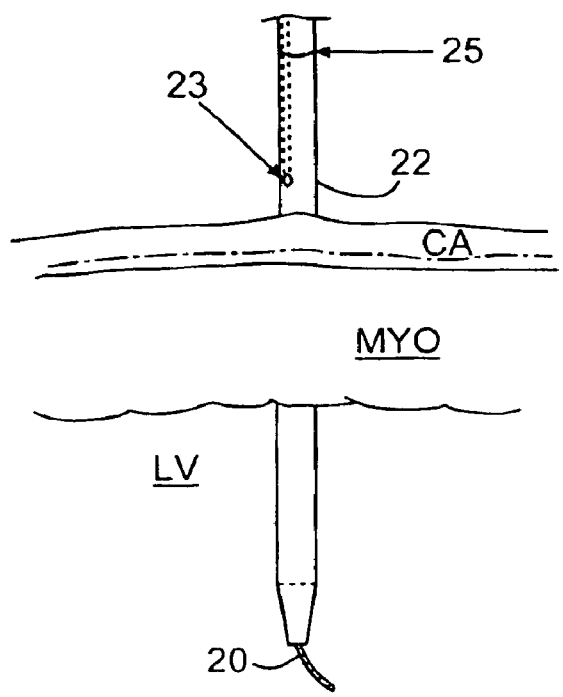
Figure 5D:
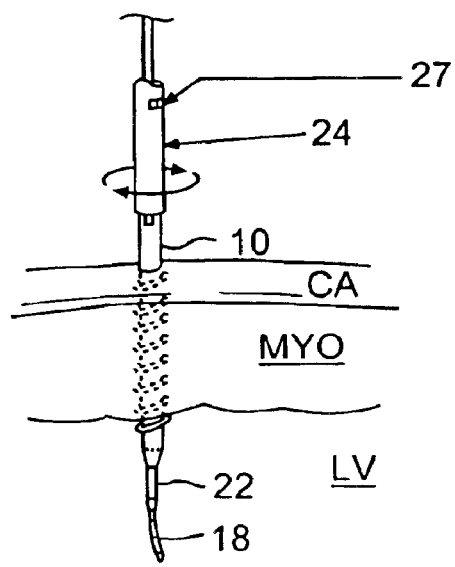

In FIGS. 5A–5D, features are shown on the components of the delivery system illustrated in FIGS. 2A, 2B, 3A and 4A to help determine the proper depth to insert the device. As shown in FIG. 5A, depth markers 19 on the needle 18 can be used to determine the thickness of the myocardium, and ensure that the device used will reach the left ventricle. As shown in FIGS. 5C and 5D, a bleed hole 23 in the dilator/introducer 22 can be used to determine the location of the lumen of the artery, and a depth marker 25 on the dilator/introducer, coupled with a window 27 in the deployment tool 24, can be used to determine when the threaded device 10 has been inserted to the proper depth.

Figure 6:
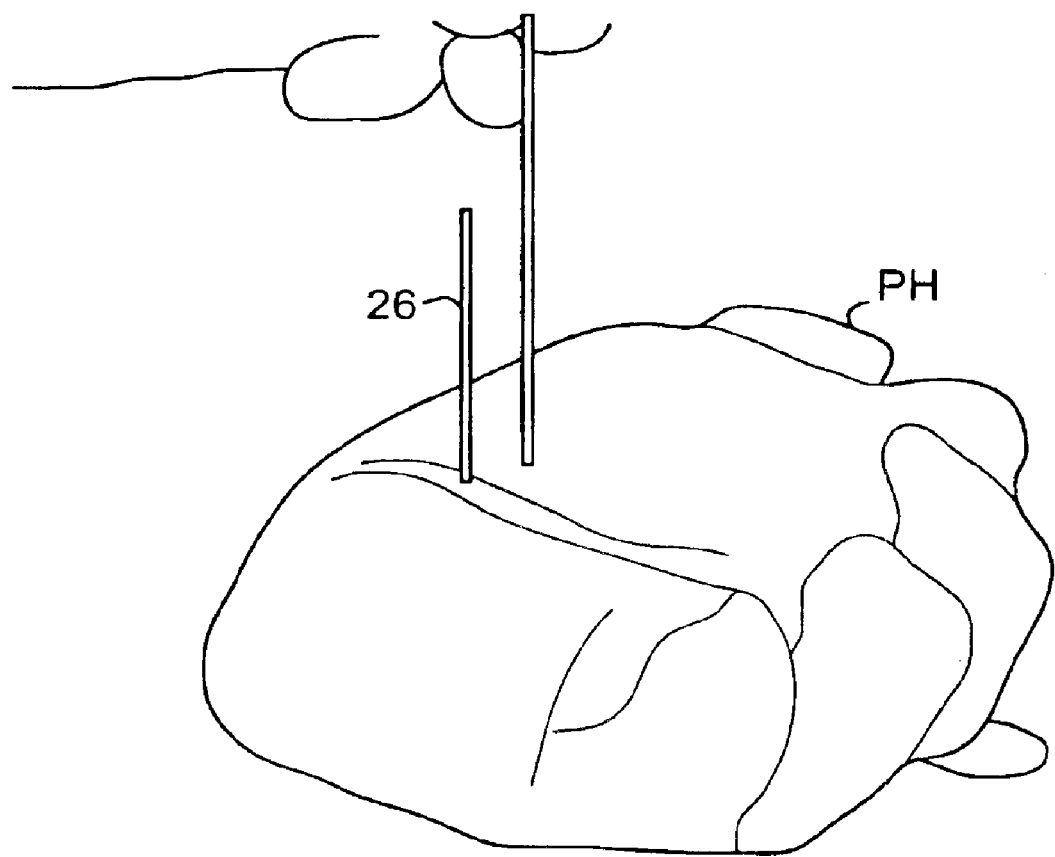
FIG. 6 is a side view of a sleeve being placed for shunt insertion.
Figure 7A:
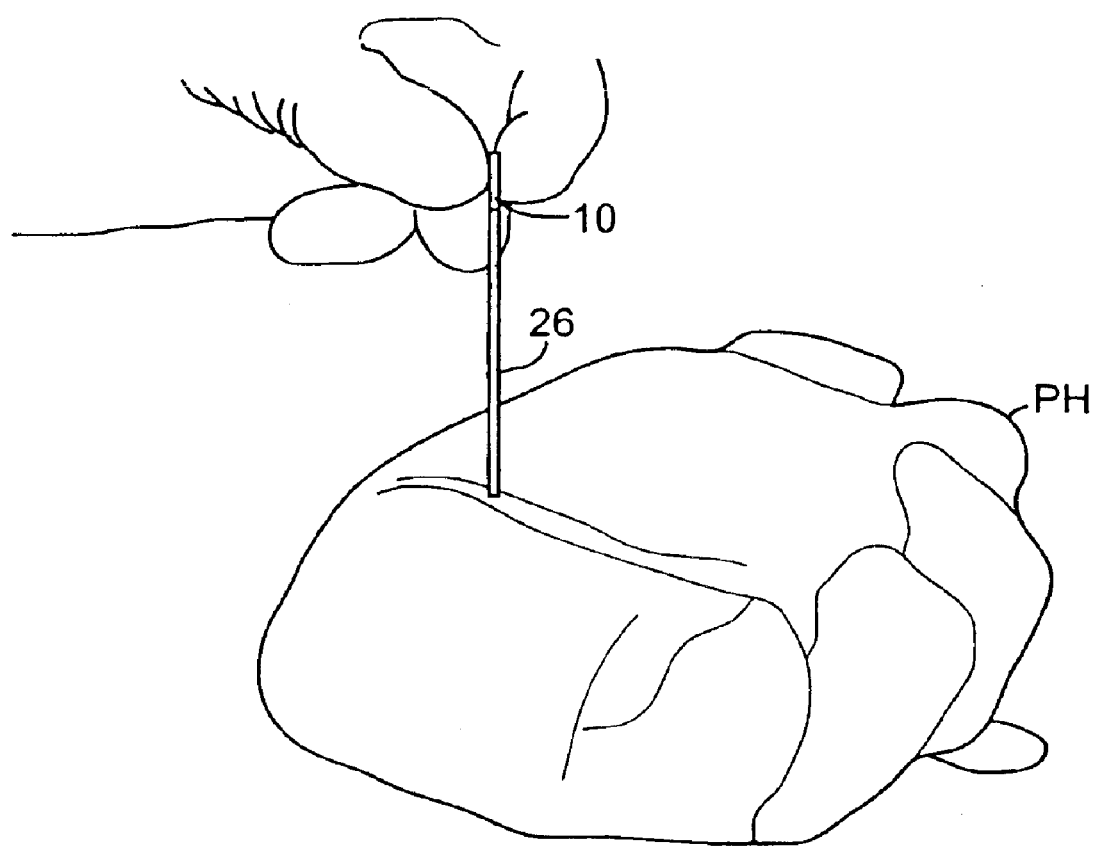
FIG. 7A is a side view of a conduit being inserted through the sleeve of FIG. 6 using a stylet.
Figure 7B:
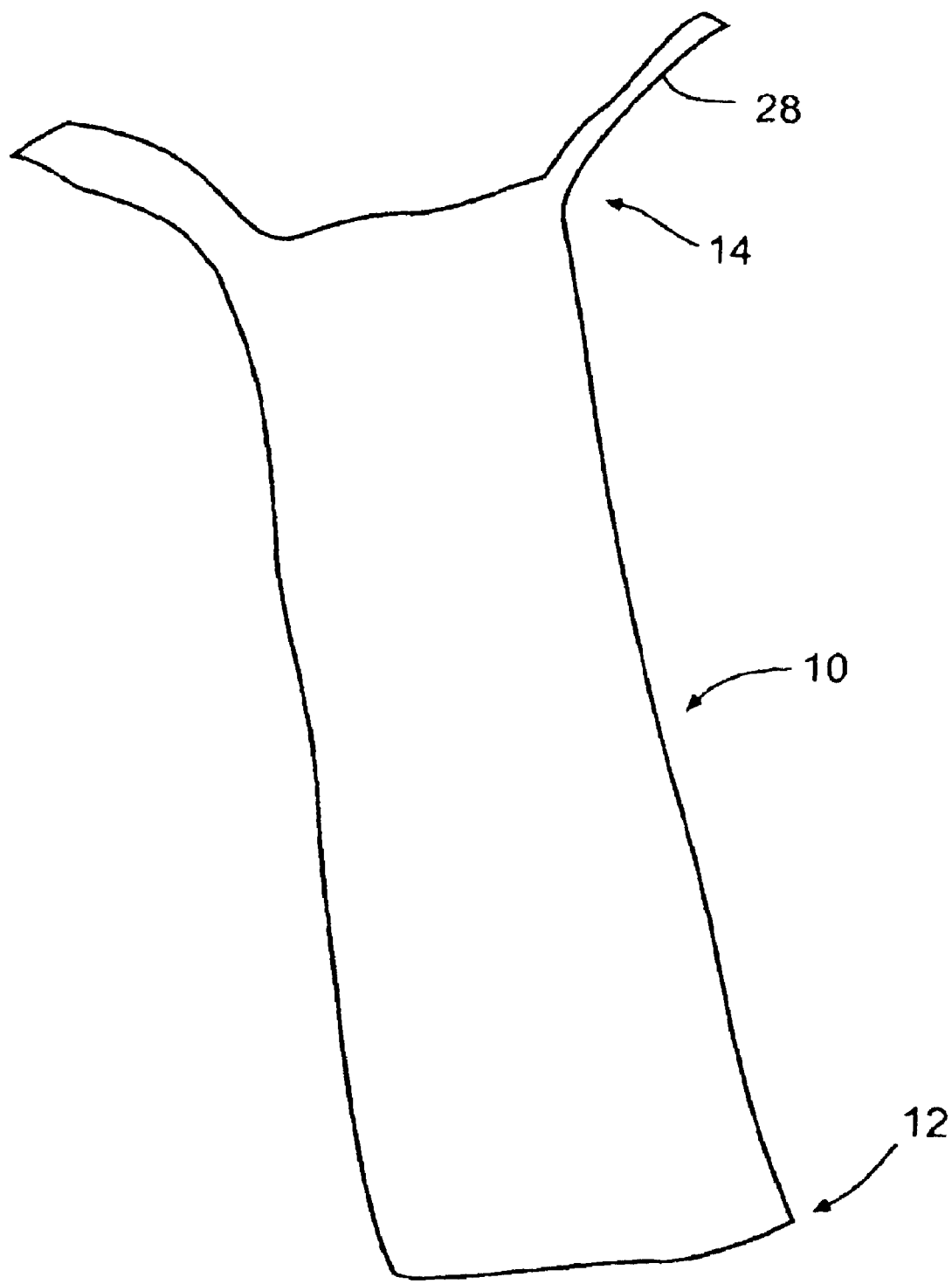
FIG. 7B illustrates the conduit of FIG. 7A having flanges.
Figure 8:
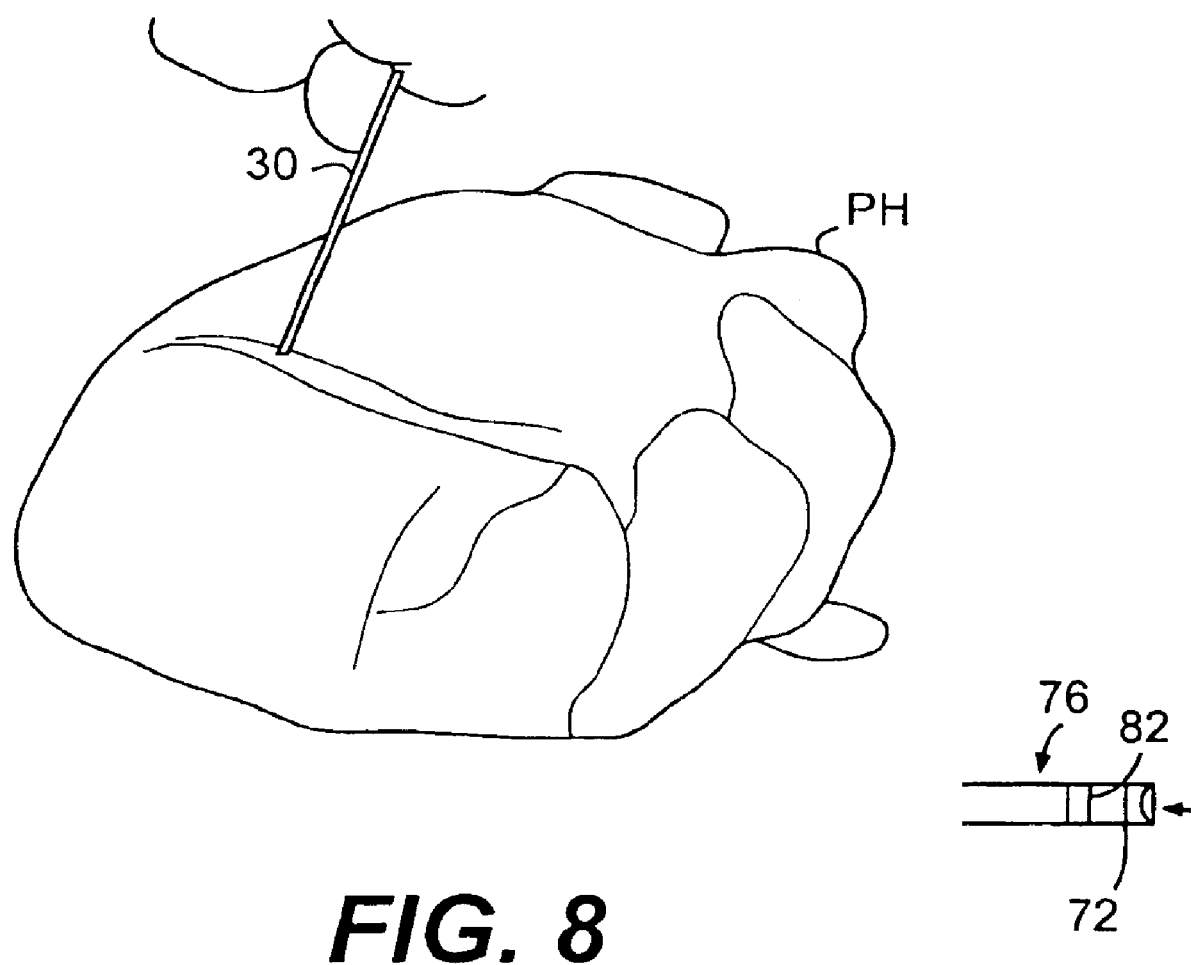
FIG. 8 is a side view of the stylet and sleeve of FIG. 7A being removed.

FIGS. 6–8 illustrate another embodiment for delivering a conduit into a patient's heart, where the conduit need not be threaded. As described and shown with respect to FIGS. 2 and 3 above, a dilator is preferably placed into the heart through the coronary artery using a needle and a guidewire. As shown in FIG. 6, a sleeve 26 is placed over the dilator and inserted into the patient's heart. The dilator is then removed.

As shown in FIG. 7A, a conduit 10 is inserted into the sleeve 26. The conduit may be in the form of a shunt, as illustrated in FIG. 7A. The conduit, as shown in FIG. 7B, may have flanges 28 on its distal end 14 which will assist in anchoring the conduit 10 to the artery. The conduit 10 is placed in the sleeve 26 by collapsing the flanges 28 into the sleeve. The conduit is advanced using a stepped stylet 30, as shown in FIG. 8, to the proper depth. This depth may be determined using an external depth measuring gauge. Holding the stylet 30 stationary, the sleeve is removed, releasing the flanges 28, preferably in the artery CA. Then the stylet is removed, leaving the conduit 10 in place.

Figure 8A:
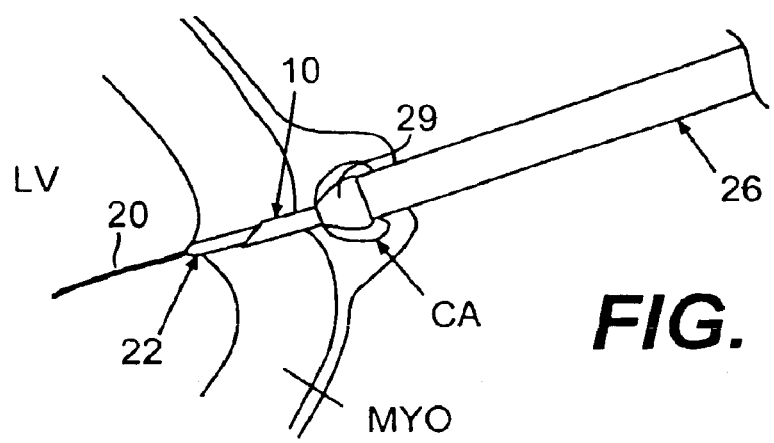
FIGS. 8A–8C are side views of a delivery system for a nonthreaded conduit illustrating a bulb feature on the outer introducer sleeve that aids in holding the artery open and achieving proper placement of the device.
Figure 8B:
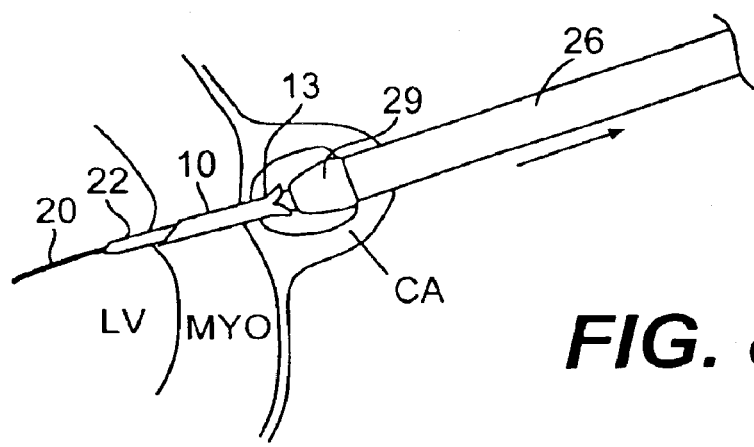
Figure 8C:
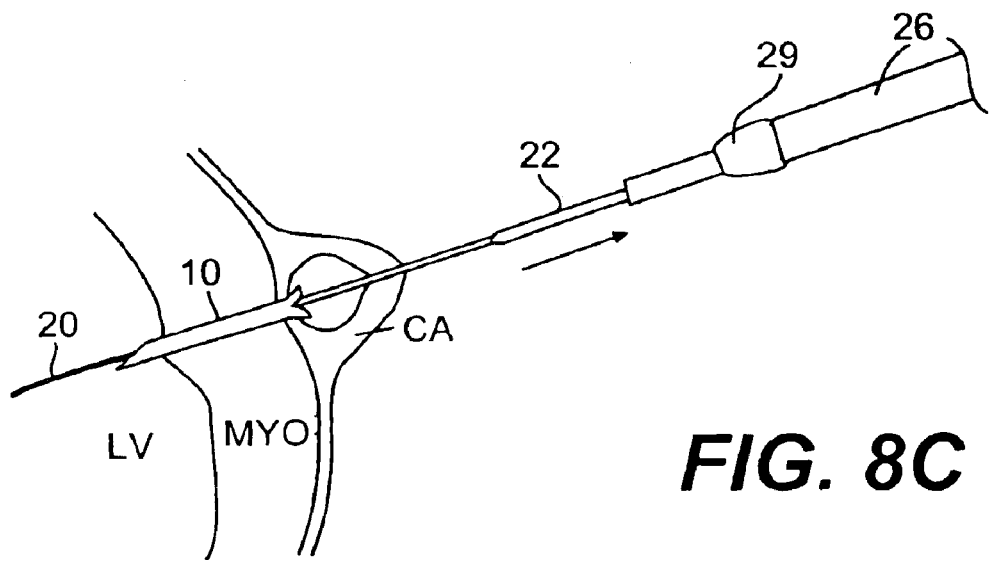

In FIGS. 8A–8C, another embodiment for inserting a non-threaded conduit is shown, wherein a bulbous feature is included on a sleeve for holding the artery open.

In this embodiment, the dilator 22, conduit 10, and sleeve 26 are assembled as shown, and inserted through the coronary artery and into the myocardium until the bulbous feature 29 is inside the lumen of the artery. The assembly is then pulled back, so that the bulbous feature 29 distends the artery. The stepped dilator 22 is then pushed into the left ventricle, advancing the conduit 10 while the sleeve 26 is held in place. The flanges 28 then deploy outside the sleeve, but inside the artery. The conduit can be advanced until the flanges bottom out on the bottom wall of the artery, then the sleeve 26 and dilator 22 can be removed. Several configurations of bulbous features can be incorporated, including a short threaded section, a balloon, or any deployable features that extend past the outer diameter (OD) of the sleeve thereby anchoring the sleeve in the lumen of the artery. It is also understood that the dilator, conduit, and sleeve can be inserted as an assembly, or individually in which case the conduit is backloaded into the sleeve after the sleeve has been placed.

It will be appreciated that various conduit configurations can be used in accordance with the embodiments of the present invention. For instance, threaded conduits, conduits with barbs and conduits with flanges may all be used. FIG. 14 shows a table of the pull out forces of various threaded conduits that may be used. FIG. 15 shows a table of the pull out forces of various barbed conduits that may be used. FIG. 16 shows a table of the push-through forces of various conduits having flanges that may be used.

Figure 9:
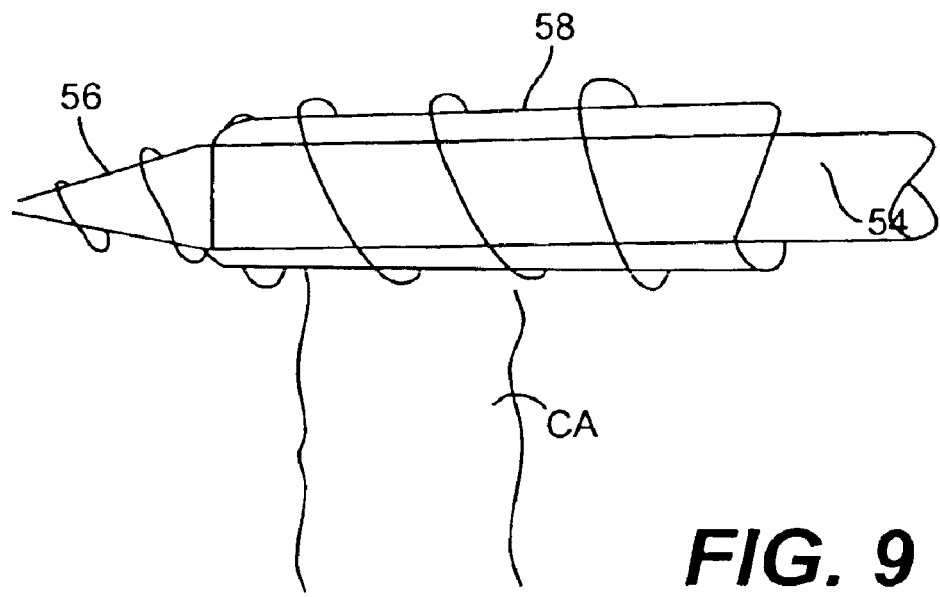
FIG. 9 is a schematic side view of a two piece threaded stylet and sleeve.

FIG. 9 illustrates a two piece threaded stylet and sleeve for delivery of a conduit. The stylet 54 is preferably threaded only on its distal tip 56 which is to be inserted into the myocardium MYO to the left ventricle. The sleeve 58 is preferably threaded over its entire body. The stylet 54 and the sleeve 58 are preferably threaded simultaneously into the myocardium. The stylet is then removed, and a conduit (not shown) for providing blood flow between the left ventricle and coronary artery is inserted through the sleeve while the threads on the sleeve hold the artery open. After insertion of the conduit the sleeve is removed. Alternatively, the threaded sleeve can function as the conduit itself.

In another embodiment, not shown, a method is provided for insertion of a curved conduit. This embodiment is useful where it is desired to provide a curved conduit between the left ventricle and coronary artery. A curved stylet is preferably inserted into the heart wall from the coronary artery to the left ventricle. A nonthreaded conduit is advanced over the curved stylet using a threaded flexible tool placed over the conduit. The threaded flexible tool is preferably attached to the conduit in order to advance the conduit over the stylet. The conduit is inserted by turning the tool until the conduit is in its desired location. In this embodiment, the conduit can be rigid or flexible.

Figure 10:
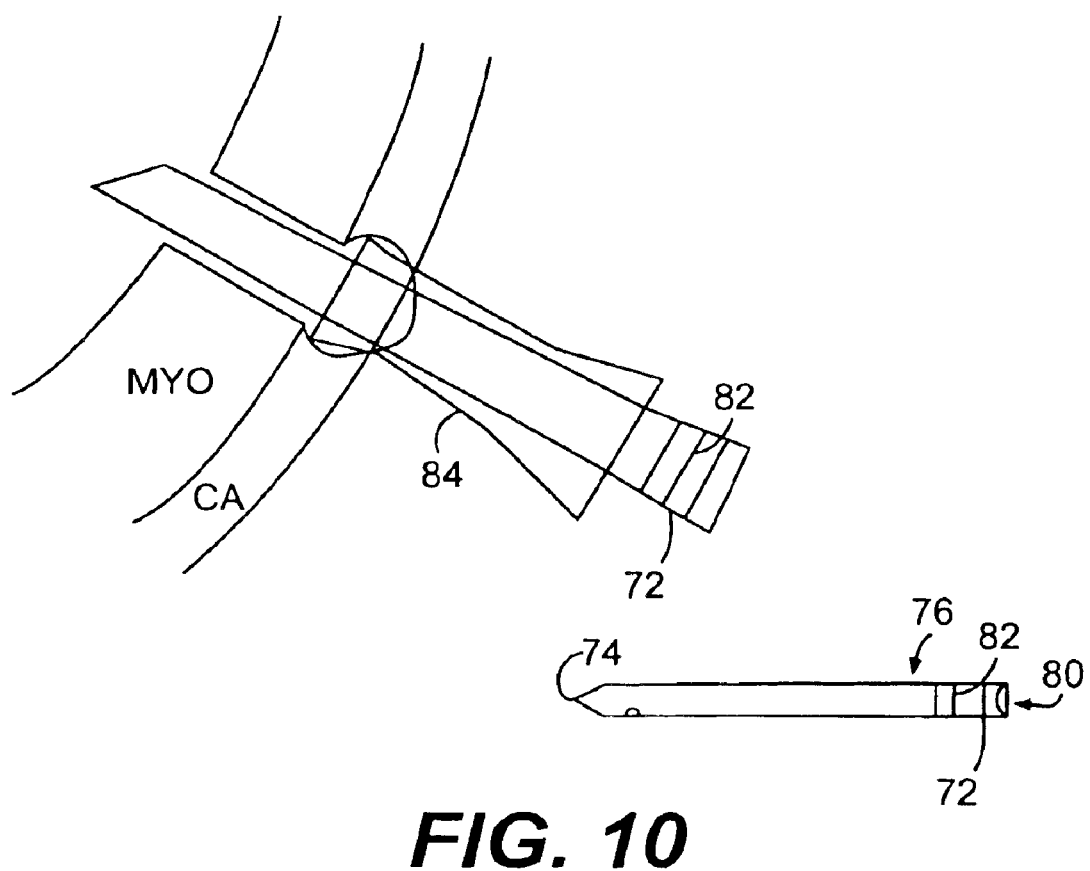
FIG. 10 is a schematic side view of a depth measuring tool.

FIG. 10 illustrates a depth measuring tool 72 for measuring the depth of the coronary artery and/or myocardium. In one embodiment, the tool 72 has a proximal end 74 with an access port 78 in fluid communication with an opening 80 on the distal end 76. Also on the distal end are markers 82 used to measure the depth of insertion of the access port 78. The proximal end is preferably tapered, and is inserted into the myocardium to the left ventricle. When the access port reaches the left ventricle, blood flows through the port and out the opening. At this point the depth of the myocardium can be determined with the markers 82. A bypass conduit 84 can then be inserted over the tool, the conduit having a length determined based on the depth d of the myocardium measured by the tool 72.

Figure 11:
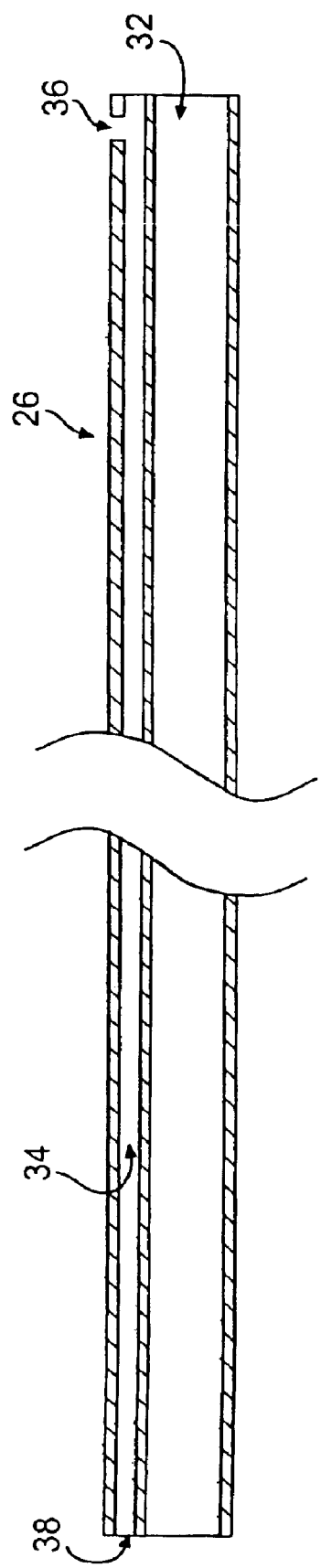
FIG. 11 is a cross-sectional view of an introducer sleeve having a side lumen for depth measurement.

In another embodiment shown in FIG. 11, a depth measuring tool may be implemented within an introducer sleeve 26 such as described above. In this embodiment, the sleeve 26 has a main lumen 32 for introduction of the conduit as described above, and also has a secondary lumen 34 in fluid communication with an access port 36 for measuring the depth of insertion of the introducer sleeve. For instance, when the sleeve 26 is inserted through the heart wall toward the left ventricle, when the sleeve reaches the left ventricle blood flows through the access port and out an opening 38 on the opposite end. Once this location is reached, markers provided on the outside of the sleeve, as described with respect to FIG. 10, are used to determine the desired size of the conduit to be inserted through the lumen 32. It will be appreciated that the depth measuring tools described above may be calibrated so that the access port is located in the coronary artery to indicate positioning therein.

Figure 12A:
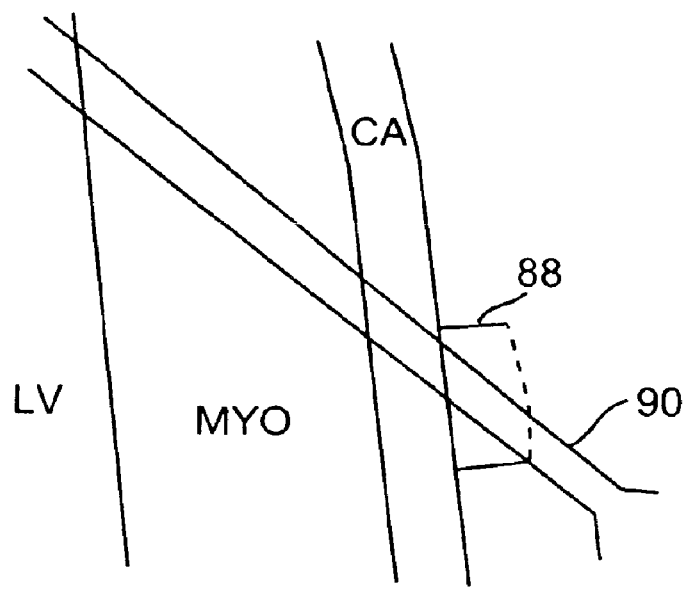
FIGS. 12A–12D are schematic side views of the delivery of a conduit from the coronary artery to the left ventricle using a dilator and introducer.
Figure 12B:
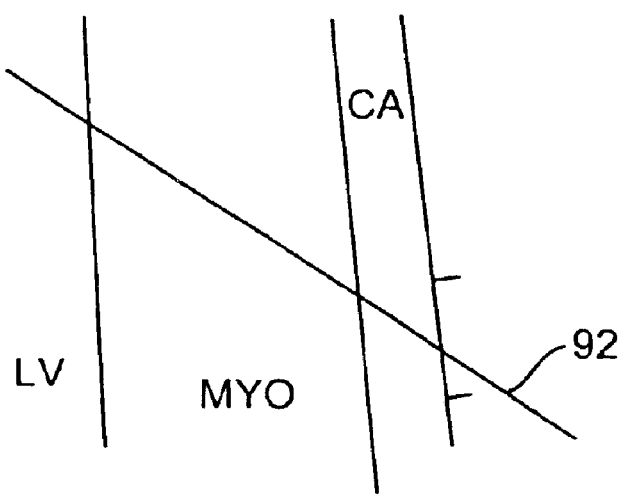
Figure 12C:
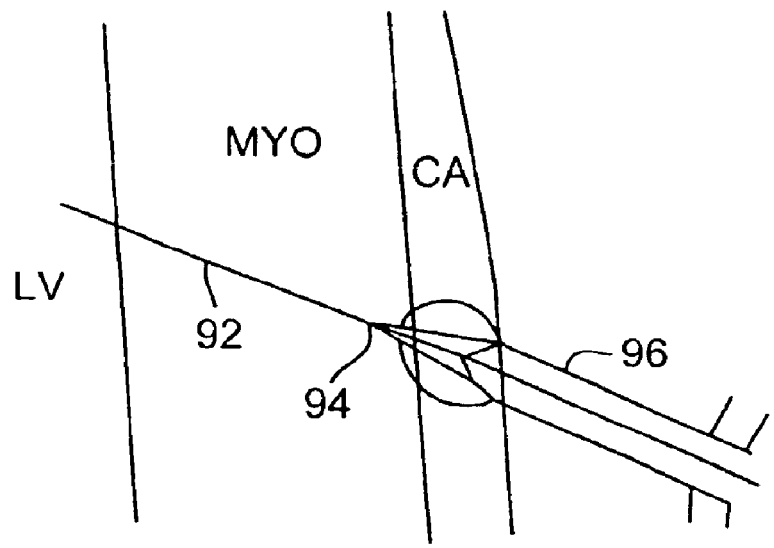
Figure 12D:
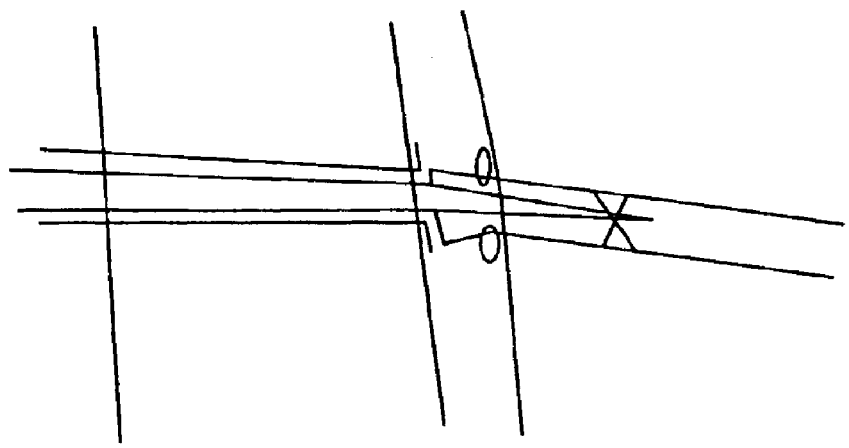

FIGS. 12A–12D illustrate the delivery of a conduit 86 using a dilator and an introducer according to another embodiment of the present invention. As shown in FIG. 12A, a template 88 is placed on the outside of the heart for positioning and a needle 90 is inserted therethrough into the coronary artery, through the myocardium and into the left ventricle. The needle 90 is hollow, and a guidewire 92 is inserted through the needle to the left ventricle, as shown in FIG. 12B. A dilator 94 is loaded onto the guidewire into the myocardium, as shown in FIG. 12C. An introducer sheath 96 is advanced over the dilator until the end of the sheath is in the artery lumen. The artery is opened, and the dilator 94 is removed. As shown in FIG. 12D, the conduit 86 is advanced through the introducer sheath, with a pusher or stylet 98 to advance the conduit into the myocardium.

Figure 13A:
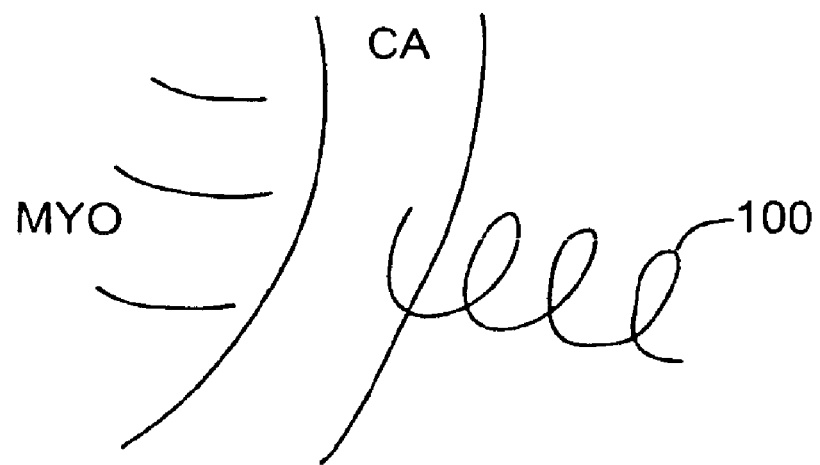
FIGS. 13A–13B are schematic side views of threads used to hold open the coronary artery.
Figure 13B:
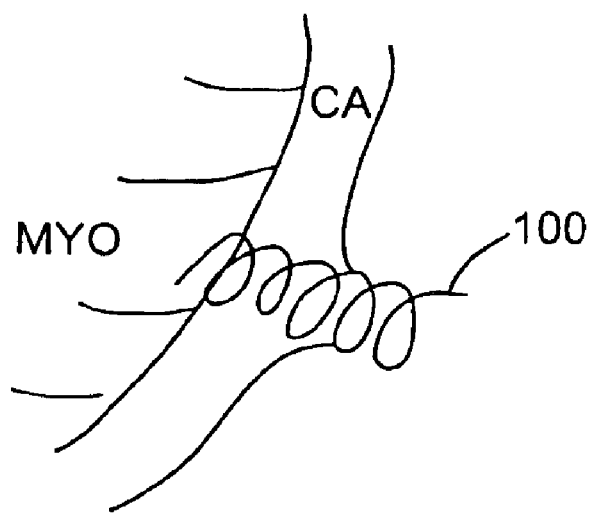

In another embodiment, shown in FIGS. 13A and 13B, coarse threads are used on a device or a tool to hold open the artery. As shown in FIG. 13A, threads 100 which are exemplarily shown are used to penetrate the outer wall of the coronary artery. These threads may be independent as shown, or may be part of a conduit or delivery tool or other member. After the threads penetrate the wall, the threads or the device on which they are attached are pulled back to open the artery. Threading continues as shown in FIG. 13B through the inner wall of the coronary artery.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. A device for measuring a depth of insertion into a heart, comprising:
    an elongate tubular body having a proximal end configured for insertion into the heart, a distal end, a first lumen extending at least partially therethrough, and a second lumen adjacent the first lumen, the second lumen being configured to receive a conduit to be placed between a heart chamber and a coronary vessel;
    an access port near the proximal end of the elongate tubular body;
    an opening near the distal end in flow communication with the access port; and
    at least one depth indication mechanism visible from the outside of the tubular body for indicating a depth of insertion of the device,
    at least one depth indication mechanism visible from the outside of the tubular body for indicating a depth of insertion of the device,
    wherein the device is configured so that when the device is inserted into the heart and reaches a blood-containing portion of the heart, blood flows through the access port and the opening and the depth indication mechanism indicates the depth of insertion of the device.

2. The device of claim 1, wherein the device is configured to permit advancement of a conduit to be placed between a heart chamber and a coronary artery.

3. The device of claim 1, wherein the first lumen extending at least partially through the elongate tubular body is a side lumen.

4. The device of claim 1, wherein the first lumen and the second lumen are side-by-side.

5. The device of claim 1, wherein the indication mechanism includes markers.

6. The device of claim 5, wherein the markers are configured so as to determine a size of a conduit configured to be implanted in the heart.

7. The device of claim 1, wherein the coronary vessel is a coronary artery.

8. The device of claim 1, wherein the blood-containing portion is the heart chamber.

9. A device for delivering a conduit to a heart wall, the device comprising:
    an elongate tubular body having a proximal end configured for insertion into the heart wall, a distal end, and a lumen extending at least partially therethrough;
    an access port near the proximal end of the elongate tubular body;
    a portion of the elongate tubular body near the distal end in flow communication with the access port, the portion permitting observation of blood flow; and
    at least one depth indication mechanism visible from the outside of the tubular body for indicating a depth of insertion of the device,
    wherein the device is configured so that when the device is inserted into the heart and reaches a blood-containing portion of the heart, blood flows through the access port and to the portion, and the depth indication mechanism indicates the depth of insertion of the device, and
    wherein the device is further configured to permit advancement of the conduit to the heart wall while the device is inserted in the heart.

10. The device of claim 9, wherein the device is configured to permit advancement of the conduit to a heart wall between a heart chamber and a coronary vessel.

11. The device of claim 10, wherein the coronary vessel is a coronary artery.

12. The device of claim 9, wherein the lumen extending at least partially through the elongate tubular body includes a side lumen.

13. The device of claim 9, wherein the portion of the elongate tubular body includes a window.

14. The device of claim 9, wherein the portion of the elongate tubular body includes an opening.

15. The device of claim 9, wherein the device is further configured to permit advancement of the conduit along the device.

16. The device of claim 9, wherein the device is further configured to permit advancement of the conduit over the device.

17. The device of claim 9, wherein the device is further configured to permit advancement of the conduit through the device.

18. The device of claim 9, wherein the distal end of the elongate tubular body is configured to be inserted through a coronary vessel.

19. The device of claim 9, wherein the device is configured to permit advancement of the conduit through a coronary vessel.

20. A device for delivering a conduit to a heart wall, the device comprising:

an elongate tubular body having a proximal end configured for insertion into the heart wall, a distal end, and a lumen extending at least partially therethrough;

an access port near the proximal end of the elongate tubular body;

a portion of the elongate tubular body near the distal end in flow communication with the access port, the portion permitting observation of blood flow;

at least one depth indication mechanism visible from the outside of the tubular body for indicating a depth of insertion of the device; and a second lumen located adjacent the lumen extending at least partially through the elongate body, the second lumen being configured to receive the conduit to be placed in the heart wall between a heart chamber and a coronary artery wherein the device is configured so that when the device is inserted into the heart and reaches a blood-containing portion of the heart, blood flows through the access port and to the portion, and the depth indication mechanism indicates the depth of insertion of the device, and wherein the device is further configured to permit advancement of the conduit to the heart wall.

* * * * *

UNITED STATES PATENT AND TRADEMARK OFFICE
CERTIFICATE OF CORRECTION

PATENT NO.   : 6,964,652 B2
DATED        : November 15, 2005
INVENTOR(S)  : Marvin Guiles et al.

It is certified that error appears in the above-identified patent and that said Letters Patent is hereby corrected as shown below:

<u>Column 7,</u>
Lines 65-67, delete.

<u>Column 8,</u>
Line 8, "artery." should read -- vessel. --.
Line 65, "distal" should read -- proximal --.

Signed and Sealed this

Twenty-fourth Day of January, 2006

JON W. DUDAS
*Director of the United States Patent and Trademark Office*